United States Patent
Miyahara et al.

(10) Patent No.: US 9,950,824 B2
(45) Date of Patent: Apr. 24, 2018

(54) PREFORM STERILIZING METHOD AND CONTENT FILLING METHOD AND SYSTEM

(71) Applicant: DAI NIPPON PRINTING CO., LTD., Tokyo (JP)

(72) Inventors: Yoshihiro Miyahara, Tokyo (JP); Hirotaka Tsuchiya, Tokyo (JP); Yoshio Nishida, Tokyo (JP)

(73) Assignee: DAI NIPPON PRINTING CO., LTD., Tokyo (JP)

( * ) Notice: Subject to any disclaimer, the term of this patent is extended or adjusted under 35 U.S.C. 154(b) by 730 days.

(21) Appl. No.: 14/385,363

(22) PCT Filed: Mar. 13, 2013

(86) PCT No.: PCT/JP2013/057024
§ 371 (c)(1),
(2) Date: Sep. 15, 2014

(87) PCT Pub. No.: WO2013/137325
PCT Pub. Date: Sep. 19, 2013

(65) Prior Publication Data
US 2015/0027088 A1   Jan. 29, 2015

(30) Foreign Application Priority Data

Mar. 14, 2012   (JP) ................. 2012-057824
Mar. 14, 2012   (JP) ................. 2012-057825
(Continued)

(51) Int. Cl.
*A61L 2/08*   (2006.01)
*B65B 55/06*   (2006.01)
(Continued)

(52) U.S. Cl.
CPC ............. *B65B 55/06* (2013.01); *A61L 2/07* (2013.01); *B29C 49/4252* (2013.01);
(Continued)

(58) Field of Classification Search
CPC ............. A61L 2/00; A61L 2/0023; A61L 2/07
(Continued)

(56) References Cited

U.S. PATENT DOCUMENTS 6,984,360 B1   1/2006   Feuilloley et al.
8,470,240 B2   6/2013   Quetel et al.
(Continued)

FOREIGN PATENT DOCUMENTS

DE   4305478   8/1994
GB   2084467   4/1982
(Continued)

OTHER PUBLICATIONS

Japanese Patent Office English Translation of the Detailed Section of JP 2009-274740.*
(Continued)

*Primary Examiner* — Monzer R Chorbaji
(74) *Attorney, Agent, or Firm* — Young & Thompson

(57) ABSTRACT

A preform is easily and promptly sterilized. Superheated steam (S) generated from water, and having a temperature of 200° C. to 500° C. and a pressure higher than atmospheric pressure is blasted to entire inner and outer surfaces of a preform (1) including a mouth portion (1a) thereof.

15 Claims, 9 Drawing Sheets

(30) Foreign Application Priority Data

Sep. 5, 2012 (JP) .................................. 2012-195459
Sep. 5, 2012 (JP) .................................. 2012-195460

(51) Int. Cl.

| | | |
|---|---|---|
| B65B 55/10 | (2006.01) | |
| B65B 3/02 | (2006.01) | |
| B67C 7/00 | (2006.01) | |
| B29C 49/42 | (2006.01) | |
| A61L 2/07 | (2006.01) | |
| B67C 3/22 | (2006.01) | |
| B29L 31/00 | (2006.01) | |
| B29C 49/06 | (2006.01) | |
| B29C 49/02 | (2006.01) | |
| B29C 49/46 | (2006.01) | |

(52) U.S. Cl.
CPC .............. *B65B 3/022* (2013.01); *B65B 55/10* (2013.01); *B67C 7/0073* (2013.01); *B29C 49/06* (2013.01); *B29C 2049/024* (2013.01); *B29C 2049/4682* (2013.01); *B29L 2031/7158* (2013.01); *B67C 2003/227* (2013.01)

(58) Field of Classification Search
USPC .......................................................... 422/26
See application file for complete search history.

(56) References Cited

U.S. PATENT DOCUMENTS

| | | |
|---|---|---|
| 2001/0010145 A1 | 8/2001 | Tawa et al. |
| 2008/0152538 A1 | 6/2008 | Quetel et al. |
| 2010/0178401 A1* | 7/2010 | Van Appeldoorn ... A23L 3/0155 426/392 |
| 2011/0311675 A1 | 12/2011 | Voth et al. |

FOREIGN PATENT DOCUMENTS

| | | | |
|---|---|---|---|
| JP | 57-86438 | 5/1982 | |
| JP | 2001-212874 | 8/2001 | |
| JP | 3780165 | 5/2006 | |
| JP | 2007-111886 | 5/2007 | |
| JP | 2008-183899 | 8/2008 | |
| JP | 2009-274740 | * 11/2009 | ............... A61L 2/18 |
| JP | 2010-202284 | 9/2010 | |
| JP | 2012-021675 | 2/2012 | |

OTHER PUBLICATIONS

International Search Report, PCT/JP2013/057024, dated May 14, 2013.

* cited by examiner

PREFORM STERILIZING METHOD AND CONTENT FILLING METHOD AND SYSTEM

TECHNICAL FIELD

The present invention relates to a method of sterilizing a preform for forming a container such as bottle and also relates to method and system for filling the container with drink or like.

BACKGROUND TECHNOLOGY

In a conventional technology, there has been provided an aseptic filling method as an inline system for forming an aseptic package by, while conveying a preform made of PET (polyethyleneterephtalate), performing a sterilization treatment by blasting a sterilizing agent gas such as hydrogen peroxide or like to the preform, molding the preform into a bottle by a blow-molding machine, filling the bottle with drink, and then capping the bottle (for example, refer to Patent Document 1)

Furthermore, there have been also provided a method in which evaporated sterilizing agent is adhered to a preform, and remaining sterilizing agent is exhausted by flame of a burner (for example, refer to Patent Document 2), and a method in which steam of a sterilizing agent is sprayed to a preform and the preform is heated and then blow-molded (for example, refer to Patent Document 3).

Furthermore, there has been also provided a method of sterilizing a preform without using any sterilizing agent. In such method, water steam is blasted into a preform to heat the preform to a temperature more than glass-transition point and maintain that temperature for a predetermined time for sterilizing the interior of the preform, and immediately thereafter, air is blasted into the preform to remove steam drain from the preform (for example, refer to Patent Document 4).

PRIOR ART DOCUMENT

Patent Document

Patent Document 1: Japanese Patent Laid-open Publication No. 2001-212874
Patent Document 2: Japanese Patent No. 3780165
Patent Document 3: Japanese Patent Laid-open Publication No. 2008-183899
Patent Document 4: Japanese Patent Laid-open Publication No. 2007-111886

SUMMARY OF THE INVENTION

Problems to be Solved by the Invention

The conventional preform sterilizing methods using the sterilizing agents provide such a problem as that the sterilizing agent may remain inside the preform. In addition, when the preform is blow-molded after the sterilization, parts or elements constituting a molding machine are liable to be corroded by the remaining sterilizing agent.

Furthermore, the conventional preform sterilizing methods using the sterilizing agents provides such a problem as that if concentration of the sterilizing agent is increased to enhance the sterilizing effect, the sterilizing agent is liable to easily remain inside the preform. In addition, there is also provided such a problem as that the parts or elements constituting the molding machine is liable to be easily corroded by the remaining sterilizing agent having high concentration.

Still furthermore, according to the conventional method in which the interior of the preform is sterilized by using steam, the problem such that the sterilizing agent remains may be solved. However, if drain of the steam remains inside the preform, such remaining steam drain may cause a reason for generation of whitening at a time of molding the preform into a container, and hence, it is required to additionally perform treatment or process for removing the drain after the sterilization, thus providing a problem. In addition, when the steam is applied to the mouth portion of the preform, the mouth portion is liable to be deformed, which may cause a degradation of sealing performance when a lid is applied to the mouth portion. Moreover, in the conventionally provided sterilizing method using water steam, it is impossible to raise temperature of the water steam, so that the surface of the preform cannot be sufficiently sterilized, thus also providing a problem.

An object of the present invention is to solve the problem mentioned above.

Means for Solving the Problem

In order to achieve the above object, the present invention adopts the following structures or configurations.

That is, the invention defined in claim 1 adopts a method for sterilizing a preform, wherein superheated steam (S) generated from water, and having a temperature of 200° C. to 500° C. and a pressure higher than atmospheric pressure is blasted to at least an inner surface of an entire surface of a preform (1) including a mouth portion (1a) thereof.

As defined in claim 2, in the preform sterilizing method of claim 1, it may be preferred that the superheated steam (S) is generated by induction-heating the water.

As defined in claim 3, in the preform sterilizing method of claim 1 or 2, it may be preferred that the sterilization of the inner surface of the preform (1) is performed by blasting the superheated steam (S) through a nozzle (7) disposed oppositely to the mouth portion (1a) of the preform (1) into the preform, and a flow rate of the superheated steam (S) is set to a level so as not to deform the mouth portion (1a) of the preform (1).

As defined in claim 4, in the preform sterilizing method of any one of claims 1 to 3, it may be preferred that the superheated steam, that was generated from the water mixed with a hydrogen peroxide of 0.5% to 15% concentration, and having a temperature of 150° C. to 500° C. and a pressure higher than atmospheric pressure is blasted to at least the inner surface of the entire surface of the preform including a mouth portion thereof.

As defined in claim 5, in the preform sterilizing method of any one of claims 1 to 4, it may be preferred that an aseptic hot air is blasted to at least the inner surface of the entire surface of the preform including a mouth portion thereof to preheat the inner surface, and the superheated steam is then blasted to at least the inner surface.

Further, the invention according to claim 6 adopts an inner content filling method including the steps of, while continuously travelling preforms (1), sterilizing at least an inner surface of each preform (1), heating the sterilized preform (1) to a temperature suitable for molding the preform, forming a container by blow-molding the preform in a blow-molding mold (12) that is also continuously travelled, filing the molded container with an inner content (a) and then sealing the container with a lid (4), wherein the sterilization of the preform (1) is performed by blasting superheated steam (S) having a temperature of 200° C. to 500° C. and a pressure higher than atmospheric pressure is blasted to at least an inner surface of an entire surface of a preform (1) including a mouth portion (1a) thereof.

As defined in claim 7, in the inner content filling method of claim 6, it may be preferred that the superheated steam, that was generated from the water mixed with a hydrogen peroxide of 0.5% to 15% concentration, and having a temperature of 150° C. to 500° C. and a pressure higher than atmospheric pressure is blasted to at least the inner surface of the entire surface of the preform including a mouth portion thereof.

As defined in claim 8, in the inner content filling method of claim 6 or 7, it may be preferred that an aseptic hot air is blasted to at least the inner surface of the entire surface of the preform including a mouth portion thereof to preheat the inner surface, and the superheated steam is then blasted to at least the inner surface.

An invention according to claim 9 adopts an inner content filling apparatus that includes: a conveying path on which preforms (1) and containers (2) are continuously travelled till each preform (1) is formed into a container (2), an inner content (a) fills each container (2), and the container (2) is sealed with a lid (4); sterilizing means that sterilizes the preform (1); a heater (10) that heats the sterilized preform (1) to a temperature suitable for a subsequent blow-molding treatment; a mold (12) that blow-molds the heated preform (1) into the container (2): a filler (35) that fill the inner content (a) into the blow-molded container: and a capper (36) that seals the container (2) filled up with the inner content, the sterilizing means, the heater, the mold, the filler and the capper being arranged along the conveying path, wherein the sterilizing means is provided with a superheated steam generator (6) that generates the superheated steam (S) having a temperature of 200° C. to 500° C. and a pressure higher than atmospheric pressure by heating water passing through a coil-shaped conductive pipe by induction heating, and a nozzle (7) that blasts the thus generated superheated steam to at least an inner surface of an entire surface of the preform (1) including a mouth portion (1a) thereof.

As defined in claim 10, in the inner content filling apparatus of 9, it may be preferred that the superheated steam generator is configured to heat water mixed with hydrogen peroxide having 0.5% to 15% concentration by induction heating using the coil-shaped conductive pipe so as to generate the superheated steam having a temperature of 150° C. to 500° C. and a pressure higher than atmospheric pressure.

As defined in claim 11, in the inner content filling apparatus of claim 9 or 10, it may be preferred to further includes preheating means that preheats the preform before the sterilizing means on the conveying path.

Effects of the Invention

According to the present invention, at least the inner surface of the entire surface of the preform (1) including the mouth portion (1a) thereof can be promptly and suitably heated and sterilized without deforming the mouth portion (1a). Moreover, since the superheated steam (S) used for the sterilization is generated from water, any problem of remaining of an chemical agent, which may be caused in a case of using the chemical agent, does not occur. In addition, since the sterilization can be achieved without generating any drain from the water steam, a process for removing the drain from the preform (1) is not needed, and hence, the speed for manufacturing the product can be improved. Further, since the temperature of the superheated steam (S) is in a range of 200° C. to 500° C., it is possible to sterilize only the surface of the preform (1) without generating deformation of the preform (1) for a short time. Furthermore, since there is no need of dropping or flowing down the drain from the inside of the preform (1), the preform (1) can be sterilized with the mouth portion (1a) being maintained in a state of directing upward in its elected posture. In addition, since the preform can be conveyed, after the sterilization treatment, for the subsequent molding treatment for molding the container (2) while maintaining its elected posture, the filling of the inner content such as drink or like can be easily performed.

Furthermore, in the present invention, in the case where the superheated steam (S), that was generated from the water mixed with a hydrogen peroxide of 0.5% to 15% concentration is blasted to the preform including a mouth portion thereof, since the superheated steam (S) is mixed with the hydrogen peroxide, the spore-forming bacteria can be also sterilized. Moreover, since the superheated steam (S) including the hydrogen peroxide is used for the sterilization, the temperature of the superheated steam to be used can be reduced and the concentration of the hydrogen peroxide to be used can be also lowered.

Furthermore, in the present invention, the aseptic hot air (H) is blasted to the preform (1) to preheat the preform in advance of the sterilizing treatment by the superheated steam (S) to preliminarily increase the temperature of the surface of the preform (1), and then, the superheated steam (S) is blasted to the preform (1). According to such process, the heating and sterilizing treatments can be easily and speedily performed, and moreover, the amount of the superheated steam (S) to be blasted can be also reduced.

Still furthermore, in the present invention, in the case where the preform (1) is sterilized by blasting the superheated steam (S), that was generated from the water mixed with a hydrogen peroxide of 0.5% to 15% concentration, and the hot air (H) is blasted to the preform (1) to preheat the preform in advance of the sterilizing treatment by the superheated steam (S) to preliminarily increase the temperature of the surface of the preform (1), and then, the superheated steam (S) is blasted to the preform (1), the heating and sterilizing treatments can be easily and speedily performed, and moreover, the amount of the superheated steam (S) to be blasted can be also reduced.

Furthermore, in the present invention, by adopting the induction heating system as the superheated steam generating means, good energy efficiency is obtainable in comparison with the heating by a general heater, thus improving the sterilizing effect.

EMBODIMENT FOR CARRYING OUT THE INVENTION

Hereunder, embodiments for carrying out present invention will be described.

<Embodiment 1>

Figure 1:
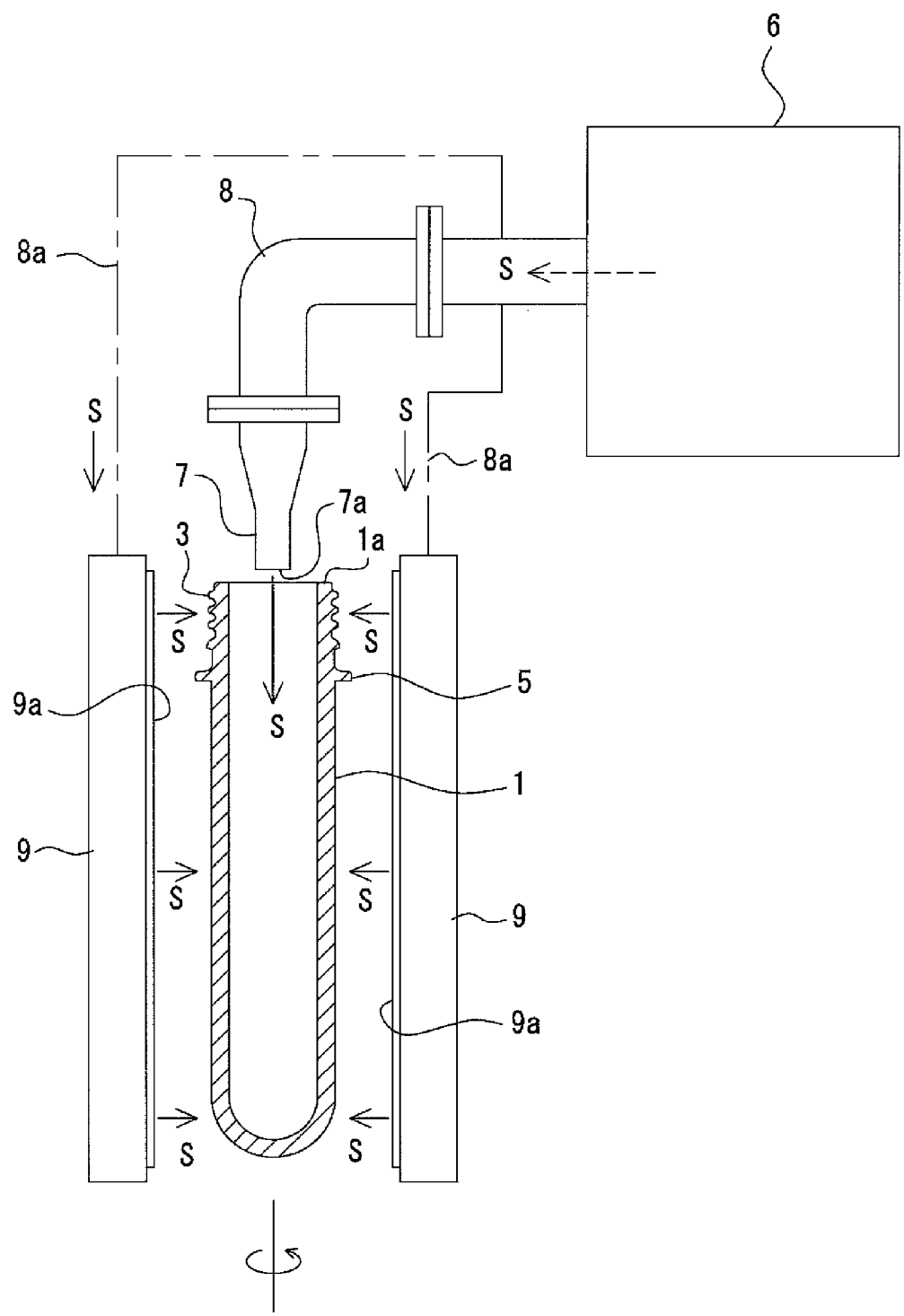
FIG. 1 is an explanation view showing a method of sterilizing the preform according to the present invention.

As shown in FIG. 1, sterilization of a preform 1 is performed by blasting a superheated steam S having a temperature of 200 to 500° C. generated from water under a pressure higher than the atmospheric pressure to entire inner and outer surfaces of the preform including a mouth portion 1a of the preform 1.

It is preferred that the superheated steam to be blasted to the preform has a temperature of 200° C. to 500° C., and more preferably, 250° C. to 400° C. In the case of the temperature range within 200° C. to 500° C., only the surface of the preform is exposed to high heat temperature to thereby sterilize spore-forming bacteria adhering to the surface of the preform can be sterilized for a short time. In a case of less than 200° C., it is required for the preform to be blasted with the superheated steam for a long time for the sufficient sterilization, which leads to highly increased temperature to a PET forming the preform, and the preform is liable to be largely deformed. On the other hand, in a case of more than 500° C., the PET forming the preform is itself highly heated for a short time, which also leads to ready deformation of the preform.

The pressure of the superheated steam to be blasted to the preform is a pressure higher than the atmospheric pressure, preferably of higher than 0.1 MPa and less than 0.3 MPa. In a case of near 0.1 MPa, even if the temperature is lowered in contact of the superheated steam to the preform, there is less possibility of condensation of the steam, but in the case of more than 0.3 MPa, the superheated steam blasted to the preform may be condensed (dewed) on the surface thereof. When the steam is condensed, there is a fear of generating whitening or like on the surface of a bottle at the time when the preform is blow-molded into the bottle.

Further, although the sterilization of the inner surface of the preform is essential, the sterilization of the outer surface may be performed by heating for the blow-molding treatment or process, that will be described hereinafter, or may be performed by adding further desired sterilization treatment after the flow-molding treatment.

Figure 3:
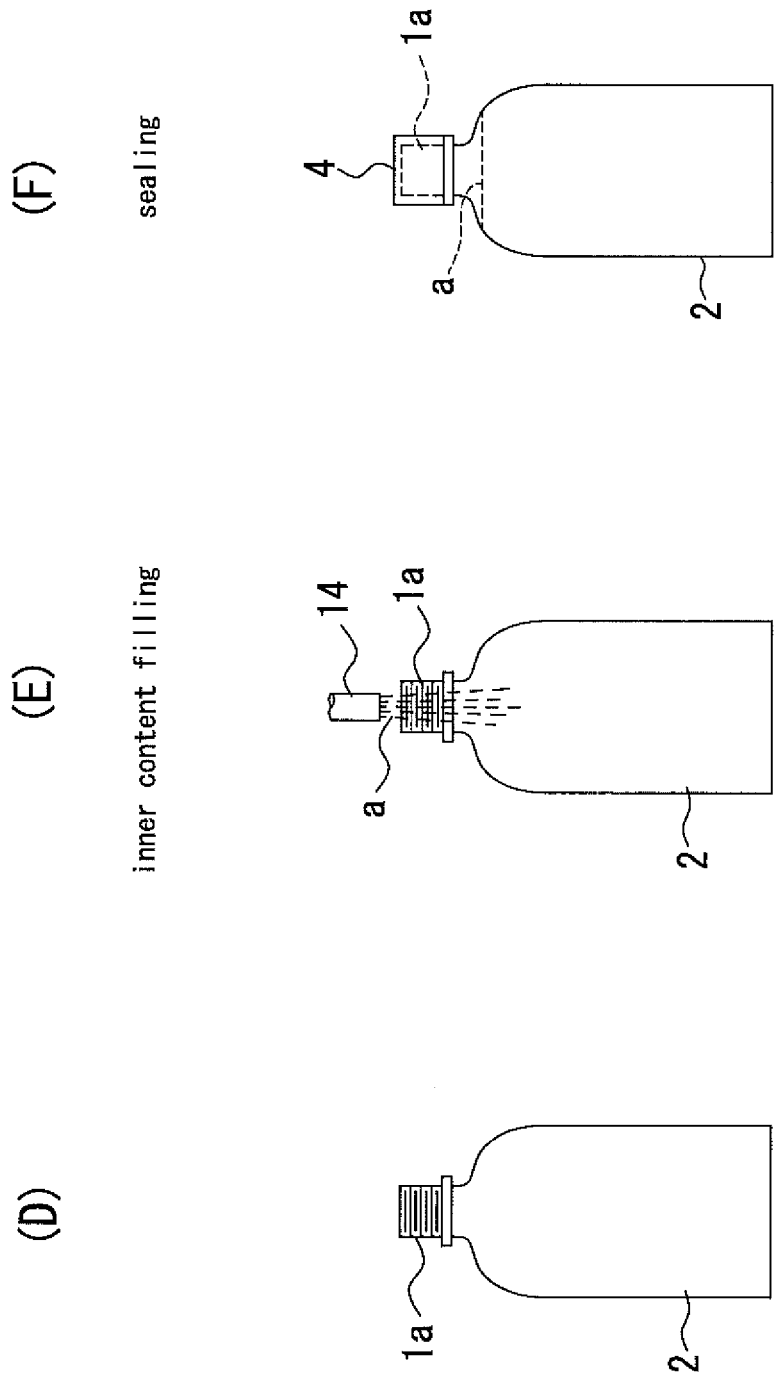
FIG. 3 is an explanatory view showing processes to a capping process after the blow-molding process.

The preform 1 is formed by injection-molding a PET into a test-tube like bottomed tubular member. The preform 1 is thereafter formed into a bottle having a desired shape (see FIG. 3 (D)), and the preform 1 is formed with a mouth portion 1a having a shape similar to that of a bottle after the molding at an initial time for the molding. A male screw portion 3 is formed on an outer peripheral surface of the mouth portion 1a at the same time as the time of molding the preform 1. As shown in FIG. 3(F), the male screw portion 3 is engageable with a female screw portion of a cap 4 to be applied to the mouth portion of the bottle 2. Below the male screw portion 3, a support ring 5 utilized at a time of filling drink in a bottle is formed.

The superheated steam S is obtainable by using a commercially sold superheated steam generator 6. More specifically, a superheated steam generator (UPSS (Trade Name of TOKUDEN Kabushiki Kaisha) may be used. This generator, though not shown, has a structure in which an induction heating coil is inserted into a central portion of a spiral of water-pass pipe composed of a spirally wound-up conductive member, water is guided into the water-pass pipe, and an A.C. voltage is applied to the induction heating coil. It may be possible to perform frequency-conversion of the A.C. voltage by an inverter so as to be energized. By the application of the A.C. voltage, the induction heating coil generates alternate magnetic flux, and an induced current passes the water-pass pipe, which is then heat-generated. The water passing inside the water-pass pipe is heated by this heat-generation and changed into saturated steam, which then becomes superheated steam S which is thereafter taken out of the water-pass pipe.

It is further to be noted that the induction heating coil may be formed from a conductive tube, and by passing water through this conductive tube, heating effect may be further enhanced.

As the superheated steam S, it is possible to obtain steam having pressure of about 0.1 MPa and temperature of 200° C. to 500° C. By adopting the induction heating method mentioned above, it is possible to change the water into superheated steam of more than 200° C. for a short time from the conduction starting time.

In FIG. 1, reference numeral 7 denotes a tubular nozzle. This tubular nozzle 7 is attached to a tip end of a conduit 8 connected to a terminal end of the water-pass pipe of the superheated steam generator 6 so as to be suspended downward, and the tubular nozzle 7 has an opening 7a directed downward.

The preform 1 is conveyed along one direction just below the circular opening 7a of the tubular nozzle 7 in a vertically elected state with the mouth portion 1a being directed upward. The conveying mode may be a continuously conveying mode in which the preforms are continuously conveyed or may be an intermittently conveying mode in which each of the preforms 1 is temporarily stopped just below the opening 7a of the tubular nozzle 7. The preform 1 is capable of being conveyed by clamping the support ring 5 thereof with a clamper, not shown.

In FIG. 1, reference numeral 9 denotes a nozzle in form of slit. This slit-shaped nozzle 9 is connected to a tip end of a branch tube 8a branched from the conduit 8 in a manner such that the slit 9a of the nozzle 9 faces a side surface of the preform 1. Preferably, a pair of slit-shaped nozzles 9 are arranged so as to sandwich the preform 1 from both side portions thereof, and the preform 1 is conveyed while rotating an axis thereof. Although it is possible to convey the preform without being rotated, in such case, it may be required for plural paired slit-shaped nozzles 9 to be arranged.

In the illustration of FIG. 1, although the slit-shaped nozzles are shown, annular-shaped nozzles such as tubular nozzles may be disposed to the side surfaces or bottom surface in an opposing manner.

When the preform 1 is sterilized, the superheated steam S is always supplied to the tubular nozzle 7 and the slit-shaped nozzle 9 from the superheated steam generator 6 so that the superheated steam S is jetted toward the preform 1 from the circular opening 7a of the tubular nozzle 7 and the slit 9a of the slit-shaped nozzle 9. The nozzle diameters, angles, preform axis and the like are preliminarily optionally set so that the jetted superheated steam S contacts the entire inner surface of the preform 1.

According to the operation mentioned above, the superheated steam S blasted from the opening 7a of the tubular nozzle 7 enters inside the preform 1 through the mouth portion 1a thereof and contacts the entire inner surface thereof to thereby sterilize general bacteria, fungus, yeast and the like adhering to the inner surface of the preform 1. Further, since such sterilization can be achieved by blasting the superheated steam S into the interior of the preform 1 for a short time, the mouth portion 1a of the preform 1 can be prevented from being excessively heated from the interior side of the preform 1 and can be hence surely prevented from being deformed.

Furthermore, the superheated steam S blasted from the slit 9a of the slit-shaped nozzle 9 contacts the entire outer surface of the preform 1, including the mouth portion 1a, now rotating around the axis thereof, thus heating and sterilizing the outer surface of the preform 1. Accordingly, general bacteria, fungus, yeast and the like adhering to the outer surface of the preform 1 can be sterilized. Further, since such sterilization can be achieved by blasting the superheated steam S into the interior of the preform 1 for a short time, the mouth portion 1a of the preform 1 can be prevented from being excessively heated from the interior side of the preform 1 and can be hence surely prevented from being deformed.

Figure 2:
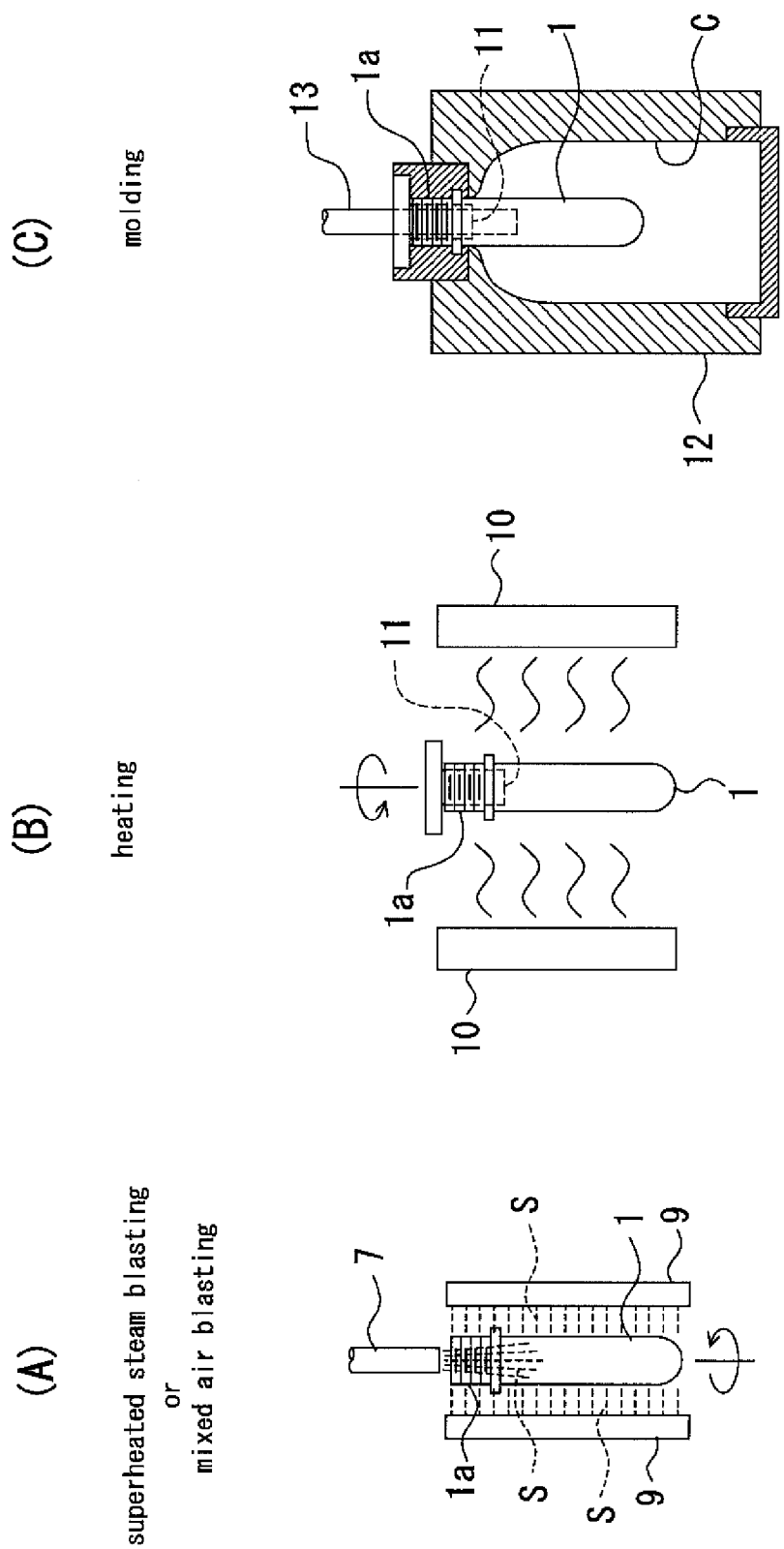
FIG. 2 is an explanation view explaining processes from a process of sterilizing the preform to a process of blow-molding the preform.
Figure 4:
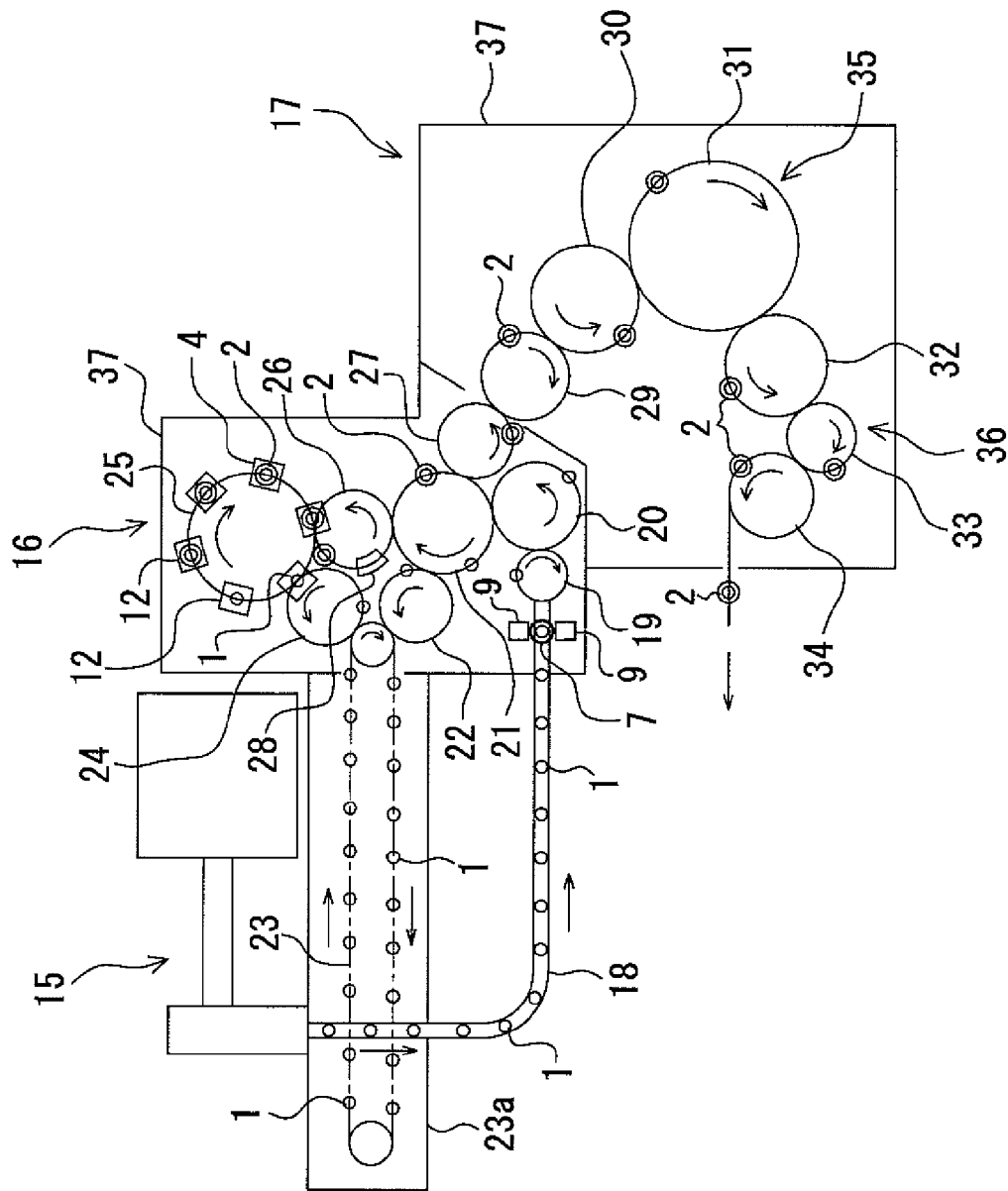
FIG. 4 is a schematic plan view showing an inner content filling machine according to the present invention.

The preform sterilizing means using the superheated steam S is incorporated in an inline system shown in FIGS. 2 to 4 to thereby produce a lot of aseptic packaging products.

In this inline system, the preforms 1 are continuously delivered at a predetermined speed, and manufactured as aseptic packaging products through processes shown in FIGS. 2 and 3.

First, as shown in FIG. 2(A), the preform 1 passes a position at which the tubular nozzle 7 and the slit-shaped nozzle 9 are disposed at a predetermined travelling speed while travelling with its vertically elected posture being maintained. During this passing, as mentioned above, the superheated steam S is blasted into the interior of the preform 1 through the mouth portion 1a and also blasted to the outer surface thereof, so that the entire surfaces including inner and outer surfaces of the preform 1 can be sterilized for a short time.

In the illustrated example, although the preform 1 is maintained in its vertically elected posture, it may be possible for the preform 1 to have its inverted posture.

Since such sterilization as described above is performed for a short time, the mouth portion 1a of the preform 1 is free from deformation and resin material forming the preform 1 is not excessively heated. In addition, since the steam drain is not dewed and does not remain on the surface of the preform 1, the bottle 2 molded in the blow-molding process performed thereafter is never whitened.

Further, the inner and outer surfaces of the preform 1 may be sterilized by alternatively shifting the tubular nozzle 7 and the slit-shaped nozzle 9 in arrangement.

As shown in FIG. 2(B), a heater 10 is disposed in a wall-like arrangement along the conveying path of the preform 1, and the preform 1 is heated, while travelling, by the heater 10 uniformly to a temperature of about 90° C. to 130° C. suitable for the subsequent blow-molding treatment.

In the heating period, a spindle 11 is inserted into the preform 1 through the mouth portion 1a thereof with the preform 1 being suspended in the elected state and rotated with the spindle 11 to be thereby uniformly heated by the heater 10.

The preform 1 heated to a temperature suitable for the blow-molding treatment is subjected to the blow-molding treatment as shown in FIG. 2(C), and then formed into the bottle 2 as a container.

A mold 12 as a blow-molding mold is continuously travelled at the same speed as the travelling speed of the preform 1, the preform 1 is clamped, the blow-molding is performed to the preform within the mold 12, and the mold 12 is thereafter opened.

The preform 1 has been heated substantially uniformly so that the entire temperature of the preform increases to a temperature range suitable for the molding treatment in the heating process shown in FIG. 2(B), and with this temperature being maintained, the preform 1 is inserted into the mold 12 together with the spindle 11 as shown in FIG. 2(C). Further, a blow nozzle 13 is inserted into the preform 1 passing the upper portion of the mold 12 and penetrating the spindle 11 in the mouth portion 1a of the preform 1.

While travelling the mold 12, for example, primary air for blowing and secondary air for blowing are subsequently blasted into the preform 1 from the blow nozzle 13, and the preform 1 is thereby swelled in the cavity C of the mold 12 into the bottle 2 as final product.

As described above, when the bottle 2 is molded into the mold 12, the mold 12 is opened while travelling, and as shown in FIG. 3(D), the product bottle 2 is taken out of the mold 12.

After the molding treatment, the bottle 2 is continuously travelled, and thereafter, as shown in FIG. 3(E), every kind of drinks a such as mineral water, tea included with catechin, carbonated drink, or like drink is filled as inner content into the bottle 2 through a filling nozzle 14, and as shown in FIG. 3(F), a cap 4 as a lid is applied to the bottle to seal the bottle 2.

Further, it may be preferred that the sterilizing effect is enhanced by sterilizing the outer surface of the bottle 2 by spraying a sterilizing agent such as hydrogen peroxide or irradiating electron ray or like to the bottle 2 after the blow-molding treatment. In a case where the inner surface of the bottle is sterilized by spraying the hydrogen peroxide, it is necessary to passively reduce concentration of the hydrogen peroxide to eliminate possibility of remaining of the hydrogen peroxide inside the bottle.

After the above treatments, the bottles 2 produced as products to be packaged are then collected and transported to markets.

An aseptic filling system (apparatus) for performing the filling method mentioned above has a configuration or structure such as shown in FIG. 4, for example.

As shown in FIG. 4, this aseptic filling system is provided with a preform supplying machine 15 for subsequently supplying bottomed tubular preforms 1, each having a mouth portion 1a (see FIGS. 1, and 2(A)), at a predetermined interval, a blow-molding machine 16 and a filling machine for filling the molded bottles 2 with the drink a and then sealing the bottles 12.

On a line from the preform supplying machine 15 to the filling machine 16, there are provided a preform conveying means for conveying the preforms 1 on the first conveying path, a mold conveying means for conveying the mold 12 (see FIG. 2(C)) having the cavity C of the shape corresponding to the product of the bottle 2 on the second conveying path connected to the first conveying path, and a bottle conveying means for conveying the bottles 2 molded by the mold 12 on the third conveying path connected to the second conveying path.

The first conveying path of the preform conveying means, the second conveying path of the mold conveying means and the third conveying path of the bottle conveying means are communicated with each other, and grippers and like members, not shown, for holding and conveying the preforms 1 and the bottles 2 are provided on these conveying paths.

The preform conveying means is provided, on its first conveying path, with a preform conveyer 18 for subsequently conveying the preforms 1 at a predetermined interval. The preform conveying means is further provided with a train of wheels 19, 20, 21 and 22 which receive the preforms 1 from the terminal end of the conveyer 18 and a conveyer 23 which receives the preforms 1 from the wheel 22 and then conveys the preforms 1.

The tubular nozzle 7 and the slit-shaped nozzle 9 for blasting the superheated steam S to the preform 1 are provided on the slightly upstream side of a portion of the preform supplying machine 15 at which the preform conveyer 18 is connected to the wheel 19. The superheated steam S is blasted toward the preforms 1 before heating (see FIGS. 1 and 2(A)) from these nozzles 14 and 16, thereby uniformly heating and sterilizing the inner and outer surfaces of the preform 1.

These nozzles and 9 may be provided on predetermined positions on the outer periphery of the wheel 22, for example, before the preform 1 reaches the conveyer 23.

The conveyer 23 includes an endless conveying chain extending longwise in the horizontal direction, and a heating unit 23a is disposed along the endless conveying chain. A number of spindles 11, one shown in FIG. 2(B), are mounted to the endless conveying chain at a constant pitch between adjacent ones. Each spindle 11 can rotate while travelling with the running of the endless conveying chain. As shown in FIG. 2(B), the spindle 11 is inserted into the preform 1, through the mouth portion 1a thereof, conveyed to the conveyer 23 from the wheel 22, and the preform 1 is held in its elected posture by the spindle 11.

The preform 1 is received by the conveyer 23 through the preform conveyer 18 and the train of the wheels 19, 20, 21, 22 and reciprocates within the heating unit 23a by the conveyer 23. The heaters 10 are attached in a spread manner on the inner wall sections of the heating unit 23a (see FIG. 2(B)), and the preform 1 is heated by the heaters 10 while being conveyed by the conveyer 23. The preform 1 rotates together with the rotation of the spindle 11 during the travelling on the conveyer 23 and is uniformly heated by the heaters 10.

The blow-molding machine 16 is provided with plural sets of the molds 12 and blow nozzles 13 (see FIG. 2(C)) receiving the preform 1 heated in the heating unit 23a of the preform supplying machine 15 and then heating and molding the preform 1 into the bottle 2.

The second conveying path of the mold conveying means described hereinbefore is arranged within the blow-molding machine 16. This second conveying path includes a train of wheels 24, 25, 26, 21 and 27. It is further to be noted that the wheel 21 is commonly used in the train of wheels 24, 25, 26, 21, 27 and the train of wheels 19, 20, 21, 22.

A plurality of such molds 12 and blow nozzles 13 are arranged around the wheel 25 and turned at a constant speed around the wheel 25 together with the rotation thereof.

When the preform 1 heated in the heating unit 23a of the preform supplying machine 15 is received by the gripper, not shown, together with the spindle 11, and is transferred to the mold 12 disposed around the wheel 25, the mold 12, now split in opened state, is closed to thereby hold the preform 1 as shown in FIG. 2(C). The preform 1 inside the mold 12 is turned around the wheel 25 together with the mold 12 and the blow nozzle 13. During such operation, the preform 1 is subjected to the blow-molding treatment with highly pressurized air blown from the blow nozzle 13, thereby being formed into a product bottle 2. As shown in FIG. 2(B), since the preform 1 is uniformly heated to the predetermined temperature by the heater 10, the blow-molding treatment can be smoothly performed.

When the preform 1 disposed inside the cavity C of the mold 12 tightly contact the inner surface of the mold 12 and the bottle 2 is formed, the mold 12 is opened at a time when the mold 12 contacts the wheel 26, and the bottle 2 and the spindle 11 are then released. Then, the bottle 2 is transferred to the gripper, not shown, of the wheel 25 from the spindle 11.

On the other hand, the spindle 11 after releasing the bottle 2 is returned to the conveyer 23 through the wheel 24 and takes a position ready for holding and conveying another preform 1.

The bottle 2 released from the blow-molding machine 16 and reaches the wheel 26 is subjected to the inspection whether the bottle is right or wrong as a molded product (i.e., defective or not in molding treatment) by an inspection device 28 provided at the outer peripheral portion of the wheel 26.

The inspection device 28 is provided with a bottle body inspection means, not shown, for discriminating whether the bottle body is right or wrong, a support ring inspection means for discriminating whether the support ring 5 (FIG. 1) of the bottle 12 is right or wrong, a bottle neck ceiling inspection means for discriminating whether the neck ceiling portion of the bottle 2 is right or wrong, and a bottle bottom inspection means for discriminating whether the bottle bottom portion is right or wrong.

The bottle body inspection means, the support ring inspection means, and the bottle neck ceiling inspection means are arranged along the outer periphery of the wheel 26.

The bottle body inspection means, the support ring inspection means, and the bottle neck ceiling inspection means are provided with lamps and cameras for photographing predetermined portions of the bottle 2, and image processing units for processing the photographed images to thereby discriminate the abnormality or like of the bottle with respect to the shape, injury, foreign material, color and the like thereof.

Further, the inspection device 28 is disposed optionally as occasion demands, and the bottle body inspection means, the support ring inspection means and the bottle neck ceiling inspection means may be selectively arranged as occasion demands.

The bottle 2, which has been judged as defective product after the inspection, is rejected from the conveying path by a rejecting device, not shown, and only acceptable product is conveyed to the wheel 27 from the wheel 26 through the wheel 21.

Further, it may be possible to additionally sterilize the outer surface of the bottle after the blow-molding treatment by spraying steam including a sterilizing agent such as hydrogen peroxide or irradiating electron ray, or possible to enhance the sterilizing effect to the inner surface of the bottle. For example, sterilization means such as sterilizing agent including steam spray device or electron ray irradiation device may be provided for the wheel 21 or 27.

The filling machine 17 is provided therein with the third conveying path of the bottle conveying means. This third conveying path includes a train of wheels 29, 30, 31, 32, 33 and 34.

A filler 35 for filling the bottle 2 with the drink a and a capper 36 for applying a cap 4 (see FIG. 3(F)) to the bottle 2 to seal the same are disposed within the filling machine 17.

It is further to be noted that since known filler and capper are usable as such filler 35 and capper 36, the explanation thereof will be omitted herein.

The filling system is surrounded by a chamber member 37 (called merely chamber hereinafter), and the interior of the chamber 37 is sectioned into an aseptic zone and gray zone. The preform supplying machine 15 and the blow-molding machine 16 are disposed in the gray zone, and the filling machine 17 is disposed in the aseptic zone, respectively.

Aseptic air sterilized in the HEPA is always blown into the gray zone, thereby conveying the bottle 2 sterilized during the molding process to the aseptic zone without being secondarily contaminated by bacteria or like.

Hereunder, the operation of the filling machine will be explained with reference to FIGS. 2 to 4.

First, the preform 1 is conveyed to the heating unit 23a by means of the conveyer 18 and the train of the wheels 19, 20, 21, 22.

Before the preform 1 enters the heating unit 23a, the superheated steam S is blasted (see FIG. 2(A)) toward the inner and outer surfaces of the preform 1 from the nozzles 7 and 9 shown in FIG. 1, thereby sterilizing the entire surface of the preform 1.

In the heating unit 23a, the preform 1 is entirely uniformly heated to a temperature of a range suitable for the subsequent molding treatment while being conveyed by the conveyer 23 (see FIG. 2(B)).

The preform 1 heated by the heating unit 23a is held by the mold 12 during the passing around the outer periphery of the wheel 25, and the preform 1 trapped inside the mold 12 is swelled into a bottle as a product in the cavity C by blasting the highly pressurized air from the blow nozzle 13 (see FIG. 2(C)).

The molded bottle 2 (see FIG. 3(D)) is taken out of the mold 12 by the gripper of the wheel 26 after opening the same, and thereafter, is inspected by the inspection device 28 to confirm whether the molding treatment is preferably performed or not.

Thereafter, the bottles 2 travel inside the filling machine 17 while being transferred to the train of the wheels 30, 31, 32, 33 and 34.

Within the filling machine 17, the bottle 2 is filled up with the drink a that has been subjected to the sterilizing treatment as shown in FIG. 3(E) by the filler nozzle 14 of the filler 35. The sterilized cap 4 is then applied to the mouth portion 1a of the bottle 2 by the capper 36, and the bottle 2 is then sealed (see FIG. 3(F)) and discharged out of the chamber 37.

As described hereinbefore, since the filler 35 and the capper 36 are known ones, the explanation of the drink filling method for the bottle 2 and the bottle sealing method will be omitted herein.

It is further to be noted that the present invention is not limited to the described embodiment and many other embodiments may be applicable. For example, containers to which the present invention is applied are not limited to the PET bottles, but the present invention is applicable to various resin containers. Furthermore, the container molding method is not limited to the injection-blow molding, but various blow-molding methods such as direct-blow molding, may be used. Moreover, conveying means for conveying the preforms and containers is not limited to the wheel conveying device shown in FIG. 4. Various conveying means capable of conveying the containers at predetermined conveying speed in the container molded order, such as belt-type conveyer, bucket-type conveyer, pneumatic-type conveyer or like, may be used.

EXAMPLE 1

Superheated steam having flow rate of 0.7 g/sec. generated by heating water by using a superheated steam generator of induction heating system was sprayed to the inner surface of each preform for a 500 mL (milliliter) PET bottle and a preform for a 2 L (litter) PET bottle from a nozzle having an inner diameter of 8 mmΦ at a blasting temperature of 300° C. for 5 sec.

In such spraying, the sterilizing effect is shown in Table 1 in an evaluation with indicating bacillus inoculated on the inner surface of the initial preform, and it was confirmed that this sterilizing effect is applicable to mineral water and the like drink.

TABLE 1

|  | B. sub. | A. nig |
| --- | --- | --- |
| For 500 mL | 3.1D | More than 6.0D |
| For 2 L | 3.0D | More than 6.0D |

In the above Table 1, term "B.sub." is an abbreviated term of "*Bacillus subtilis*", and "A.nig." is an abbreviated term of "*Aspergillus niger*". "D" is a D-valve indicating the sterilizing effect.

Further, an experiment result of deformed amount of the inner diameter of the mouth portion of the preform indicated no problem for maintaining the sealing performance of a cap as shown in the following Table 2.

TABLE 2

|  | Before Blasting Of Superheated Steam | After Blasting Of Superheated Steam |
| --- | --- | --- |
| For 500 mL | 21.77 mm | 21.75 mm |
| For 2 L | 21.75 mm | 21.71 mm |

EXAMPLE 2

Superheated steam having flow rate of 0.7 g/sec. generated by heating water by using a superheated steam generator of induction heating system was sprayed to the inner surface of each preform from a nozzle having an inner diameter of 8 mmΦ at a blasting temperature in a range of 180° C. to 550° C. for 1o to 3 sec., respectively, toward the inner surfaces of the preforms for 500 mL PET bottles.

The sterilizing effect and the deformation of the inner diameter of the preform obtained by such superheated steam spray is shown in the following Table 3.

TABLE 3

| Blasting Temperature (° C.) | Blasting Time (sec.) | Sterilizing Effect | Deformation |
| --- | --- | --- | --- |
| 180 | 10 | X | X |
| 250 | 6 | ○ | ○ |

TABLE 3-continued

| Blasting Temperature (° C.) | Blasting Time (sec.) | Sterilizing Effect | Deformation |
|---|---|---|---|
| 350 | 4 | ○ | ○ |
| 450 | 3 | ○ | ○ |
| 550 | 3 | ○ | X |

Further, it is to be noted that, in the above Table 3, the sterilization effect is shown with [○] (good) in the case where the D-value with respect to *Bacillus subtilis* is not less than 3, in the case where the D-value with respect to *Aspergillus niger* is not less than 6, and the other cases are shown with [X] (not good). With respect to the deformation of the inner diameter, in the case where the inner diameter of the preform is deformed by less than 0.05 mm is shown [○] (good), and the other cases are shown with [X] (not good).

<Embodiment 2>

Hereunder, the second embodiment 2 of the present invention will be explained with reference to FIGS. 1 to 4 used for the explanation of the first embodiment 1.

As shown in FIG. 1, the sterilization of the preform 1 is performed by blasting the superheated steam S, generated from water with which hydrogen peroxide having concentration of 0.5% to 25% is mixed, having pressure higher than atmospheric pressure and having temperature of 150 to 500° C., to the entire surface of the preform 1, i.e., entire inner and outer surfaces of the preform 1 including the mouth portion 1a thereof.

A temperature for blasting the superheated steam S to the preform 1 is preferably of 150° C. to 500° C., and more preferably, 250° C. to 400° C. Within the temperature range of 150° C. to 500° C., only the surface of the preform is exposed to high temperature, and thereby, fungus or like adhering to the surface of the preform 1 can be sterilized for a short time. In the case of the temperature of the superheated steam S of less than 150° C., long time blasting of the superheated steam S is required for the sterilization, which will result in temperature increasing of the PET itself constituting the preform 1, which may lead to deformation of the preform. In the case of more than 500° C., the temperature of the PET will be increased for a short time, which will lead to easy deformation of the preform 1.

A pressure of the superheated steam S to be blasted to the preform 1 is higher than the atmospheric pressure, and is preferably more than 0.1 MPa and less than 0.3 MPa. In a case where this pressure is near 0.1 MPa, even if the superheated steam S contacts the preform and the temperature thereof is lowered, there is less possibility of condensation (bedewing), and in a case where this pressure is more than 0.3 MPa, when the superheated steam S is blasted to the preform 1, the condensation thereof may be formed on the surface of the preform 1. When such condensation is formed, there may cause a fear of generating whitening to the surface of the bottle 2 at the time of blow-molding the preform into a bottle or like.

It is preferred that the hydrogen peroxide to be mixed with the water has concentration of 0.5 to 15%, and more preferably, 1 to 10%. In the case of less than 0.5%, the sterilizing power against the spore-forming bacteria is insufficient, and in the case of more than 15%, the hydrogen peroxide will remain much.

The preform may be made of resins other than PET such as high density polyethylene, polycarbonate or like. In the case when the preform is made of the high density polyethylene or polycarbonate, it is desired to sterilize the preform with the superheated steam of the temperature in the range mentioned above.

Further, although the sterilization of the inner surface of the preform is essential, the sterilization of the outer surface may be performed by heating the preform for the blow-molding treatment, that will be described hereinafter, or may be performed by additionally performing further desired sterilization treatment after the flow-molding treatment.

As the preform 1, one having same structure as that used in the first embodiment will be usable.

The superheated steam S is obtainable by using the superheated steam generator used in the first embodiment. This generator, though not shown, has a structure in which water mixed with the hydrogen peroxide having 0.5 to 15% concentration is guided into the water-pass pipe and, and an A.C. voltage is applied to the induction heating coil. By the application of the A.C. voltage, the induction heating coil generates alternate magnetic flux, and an induced current passes the water-pass pipe, which is then heat-generated. The water, mixed with the hydrogen peroxide having 0.5 to 15% concentration, passing inside the water-pass pipe is heated by this heat-generation and changed into saturated steam, which then becomes superheated steam S which is thereafter taken out of the water-pass pipe.

As the superheated steam S, it is possible to obtain steam having pressure of about 0.1 MPa and temperature of 150 to 500° C. By adopting the induction heating method mentioned above, it is possible to change the water mixed with the hydrogen peroxide having 0.5% to 15% concentration into superheated steam of the temperature 150° C. to 500° C. for a short time from the conduction starting time.

When the preform 1 is sterilized, the superheated steam S generated from the water mixed with the hydrogen peroxide having 0.5% to 15% concentration is always supplied to the tubular nozzle 7 or slit-shaped nozzle 9, and is jetted toward the entire surface of the preform 1 through the circular opening 7a of the tubular nozzle 7 and the slit 9a of the slit-shaped nozzle 9. The nozzle diameters, angles, preform axis and the like are preliminarily optionally set so that the jetted superheated steam S contacts the entire inner surface of the preform 1.

According to the operation mentioned above, the superheated steam S blasted from the opening 7a of the tubular nozzle 7 enters inside the preform 1 through the mouth portion 1a thereof and contacts the entire inner surface of the preform to thereby sterilize general bacteria, fungus, yeast and the like adhering to the inner surface of the preform 1 by the heat and the hydrogen peroxide. Further, since such sterilization can be achieved for a short time by blasting the superheated steam S into the interior of the preform 1, the mouth portion 1a of the preform can be prevented from being excessively heated from the interior side of the preform 1 and can be hence surely prevented from being deformed.

Furthermore, the superheated steam S blasted from the slit 9a of the slit-shaped nozzle 9 contacts the entire outer surface of the preform 1, including the mouth portion 1a, now rotating around the axis thereof, thus also heating and sterilizing the outer surface of the preform 1. Accordingly, general bacteria, fungus, yeast and the like adhering to the outer surface of the preform 1 can be sterilized by the heat and the hydrogen peroxide. Further, since such sterilization can be achieved for a short time by blasting the superheated steam S into the interior of the preform 1, the mouth portion 1a of the preform can be prevented from being excessively heated from the interior side of the preform 1 and can be hence surely prevented from being deformed.

The preform sterilizing means using the superheated steam S is incorporated in an inline system shown in FIGS. 2 and 3 to thereby produce a large amount of aseptic packaging products.

In this inline system, the preforms 1 are continuously delivered at a predetermined speed, and manufactured as aseptic packaging products through processes or treatments shown in FIG. 2.

First, as shown in FIG. 2(A), the preform 1 passes a position at which the tubular nozzle 7 and the slit-shaped nozzle 9 are disposed at a predetermined travelling speed while travelling with its vertically elected posture being maintained. During this passing, as mentioned above, the superheated steam S is blasted into the interior of the preform 1 through the mouth portion 1a thereof and also blasted to the outer surface thereof, so that the entire surfaces including inner and outer surfaces of the preform 1 can be sterilized for a short time.

In the illustrated example, although the preform 1 is maintained in its vertically elected posture, it may be possible for the preform 1 to have its inverted posture.

Since such sterilization as described above is performed for a short time, the mouth portion 1a of the preform 1 is free from deformation and resin material forming the preform is not excessively heated. In addition, since steam drain is not dewed and does not remain on the surface of the preform 1, the bottle 2, that is molded in the blow-molding process performed thereafter, is never whitened.

Further, the inner and outer surfaces of the preform 1 may be sterilized by alternatively arranging the tubular nozzle 7 and the slit-shaped nozzle 9 in the manner shifted in positions.

As shown in FIG. 2(B), a heater 10 is disposed in a wall-like arrangement along the conveying path of the preform 1, and the preform 1 is heated, while travelling, by the heater 10 uniformly to a temperature of about 90° C. to 130° C. suitable for the subsequent blow-molding treatment.

In the heating period, a spindle 11 is inserted into the preform 1 through the mouth portion 1a thereof to be suspended in the elected state and rotated with the spindle 11 to be thereby uniformly heated by the heater 10.

The preform 1 heated to a temperature suitable for the blow-molding treatment is subjected to the blow-molding treatment as shown in FIG. 2(C), and then formed into the bottle 2 as a container.

A mold 12 as a blow-molding mold is continuously travelled at the same speed as the travelling speed of the preform 1, the preform 1 is clamped, the blow-molding is performed to the preform within the mold 12, and the mold 12 is thereafter opened.

The preform 1 has been heated substantially uniformly so that the entire temperature of the preform increases to a temperature range suitable for the molding treatment in the heating process shown in FIG. 2(B), and with this temperature being maintained, the preform 1 is inserted into the mold 12 together with the spindle 11 as shown in FIG. 2(C). Further, the blow nozzle 13 is inserted into the preform 1 passing the upper portion of the mold 12 and penetrating the spindle 11 in the mouth portion 1a of the preform 1.

During the travelling of the mold 12, for example, primary air for blowing and secondary air for blowing are subsequently blasted into the preform 1 from the blow nozzle 13, and the preform 1 is thereby swelled in the cavity C of the mold 12 into the bottle 2 as final product.

As described above, when the bottle 2 is molded into the mold 12, the mold 12 is opened while being travelled, and as shown in FIG. 3(D), the product bottle 2 is taken out of the mold 12.

After the molding treatment, the bottle 2 is continuously travelled, and thereafter, as shown in FIG. 3(E), the drink a for example, mineral water, is filled into the bottle 2 through a filling nozzle 14, and as shown in FIG. 3(F), the bottle 2 is then sealed with a cap 4 as a lid.

Further, it may be preferred that the sterilizing effect is enhanced by sterilizing the outer surface of the bottle 2 by the spray of a sterilizing agent such as hydrogen peroxide or irradiation of electron ray or like to the bottle 2 after the blow-molding treatment. In a case where the inner surface of the bottle 2 is sterilized by the hydrogen peroxide, it is necessary to passively reduce concentration of the hydrogen peroxide to eliminate possibility of remaining of the hydrogen peroxide inside the bottle 2.

After the above treatments, the bottles 2 produced as product to be packaged are collected and transported to markets.

A filling system for carrying out the filling method described above may be constructed as shown in FIG. 4 as like as the first embodiment.

The superheated steam S generated from water mixed with the hydrogen peroxide having 0.5 to 15% concentration is blasted, instead of the superheated steam used in the first embodiment, toward the preform 1 from the tubular nozzle 7 and the slit-shaped nozzle 9 provided on the slightly upstream side of a portion of the preform supplying machine 15 at which the preform conveyer 26 is connected to the wheel 27 (see FIGS. 1 and 3(A)), thereby uniformly sterilizing the inner and outer surfaces of the preform 1.

EXAMPLE 3

Superheated steam generated from water mixed with hydrogen peroxide having 3.0% concentration was heated and generated by a superheated steam generator of induction heating system and then blasted for 5 second toward respective surfaces of preforms for 500 mL PET bottle and 2 L PET bottle through a nozzle having inner diameter of 8 mmφ at flow rate of 0.7/sec. with blasting temperature of 300° C.

The sterilizing effect by the blasting of such superheated steam is shown in the following Table 4 in an evaluation with indicating bacillus inoculated on the inner surface of the preform, and it was found that such sterilizing effect is suitable for the filling of every drink such as milk, tea, flutes, carbon drink, sport drink, mineral water and the like drinks.

TABLE 4

|  | B. sub. | A. nig |
| --- | --- | --- |
| For 500 mL | 6.0D | More than 6.0D |
| For 2 L | 5.8D | More than 6.0D |

In the above Table 4, term "B.sub." is an abbreviated term of "Bacillus subtilis", and "A.nig." is an abbreviated term of "Aspergillus niger". "D" is a D-valve indicating the sterilizing effect.

Further, an experiment result of deformed amount of the inner diameter of the mouth portion of the preform indicated no problem for maintaining the sealing performance of a cap as shown in the following Table 5.

TABLE 5

|  | Before Blasting Of Superheated Steam | After Blasting Of Superheated Steam |
|---|---|---|
| For 500 mL | 21.77 mm | 21.76 mm |
| For 2 L | 21.75 mm | 21.73 mm |

EXAMPLE 4

Water mixed with the hydrogen peroxide was heated by a superheated steam generator of induction heating system to thereby generate the superheated steam, which was then splayed to the inner surface of each preform for 500 mL PET bottle from a nozzle having inner diameter of 8 mmΦ at for 10 to 3 seconds at flow rate of 0.7 g/sec. with temperature in a range of 120° C. to 550° C.

The sterilizing effect, the deformation of the inner diameter of the preform, and remaining amount of the hydrogen peroxide are shown in the following Table 6.

TABLE 6

| Hydrogen Peroxide Concentration (%) | Blasting Temperature (° C.) | Blasting Time (second) | Sterilizing Effect | Deformation | Remaining Hydrogen Peroxide |
|---|---|---|---|---|---|
| 5 | 120 | 10 | ○ | ○ | ○ |
| 5 | 180 | 7 | ○ | ○ | ○ |
| 3 | 250 | 6 | ○ | ○ | ○ |
| 3 | 350 | 4 | ○ | ○ | ○ |
| 2 | 450 | 3 | ○ | ○ | ○ |
| 2 | 550 | 3 | ○ | X | ○ |
| 0.2 | 300 | 5 | X | ○ | ○ |
| 20 | 300 | 5 | ○ | ○ | X |

Further, it is to be noted that, in the above Table 6, the sterilization effect is shown with [○] (good) in the case where the D-value with respect to *Bacillus subtilis* is not less than 5, in the case where the D-value with respect to *Aspergillus niger* is not less than 6, and the other cases are shown with [X] (not good). With respect to the deformation of the inner diameter, in the case where the inner diameter of the preform is deformed by less than 0.05 mm is shown with [○] (good), and the other cases are shown with [X] (not good). With respect to the remaining hydrogen peroxide, water filled bottles after molding the preforms into the bottles and remaining amounts of the hydrogen peroxide dissolved into the water were measured. In such measurement, cases in which the remaining amount is less than 0.5 ppm are shown with [○] (good) and the other cases are shown with [X] (not good).

<Embodiment 3>

Hereunder, the third embodiment 3 of the present invention will be explained.

Figure 5:
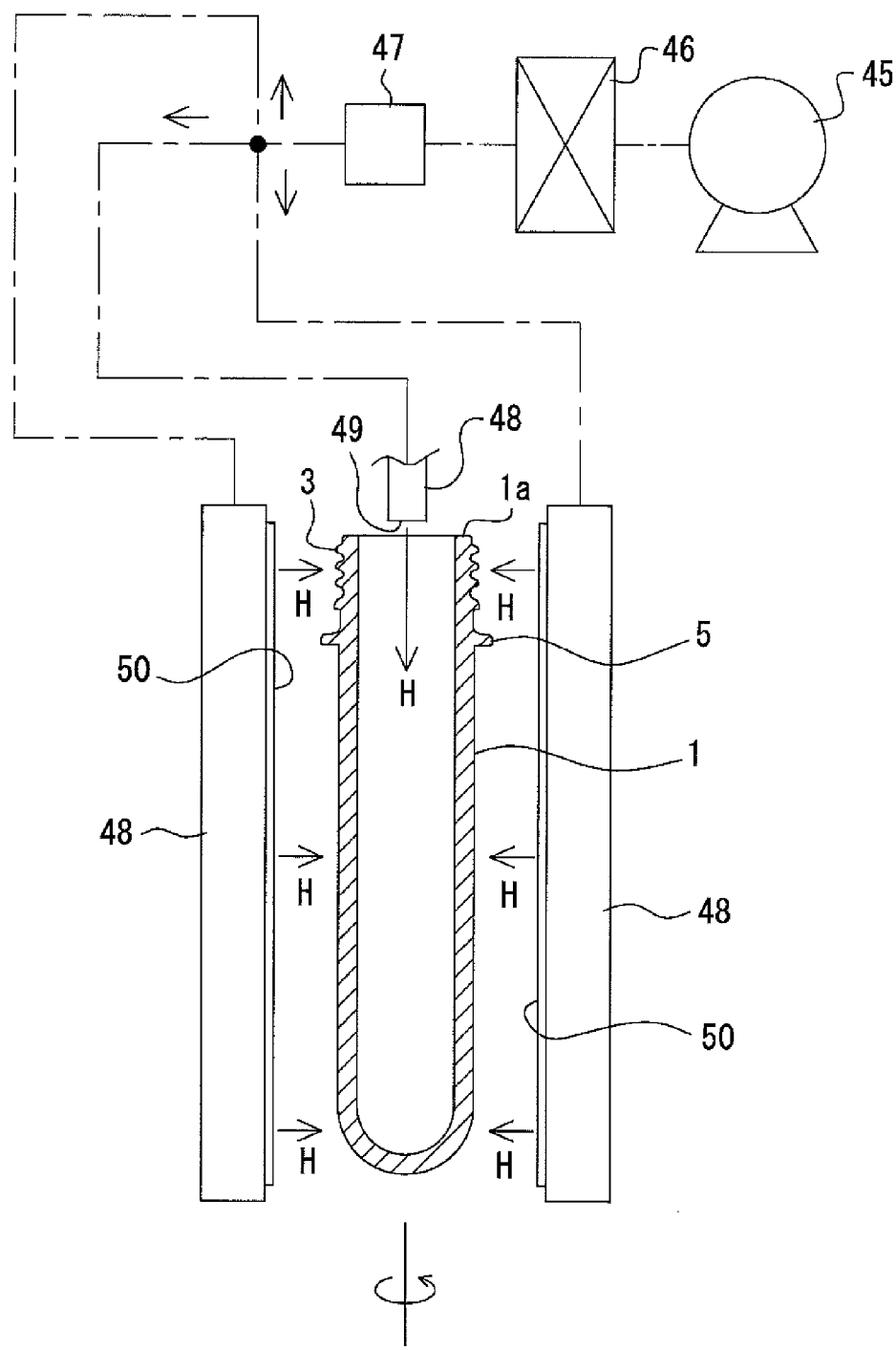
FIG. 5 is an explanatory view showing a preform preheating section.

As shown in FIG. 5, the preform 1 is formed as a tubular bottomed member having a test-tube shape as like as those in the first and second embodiments 1 and 2.

Figure 6:
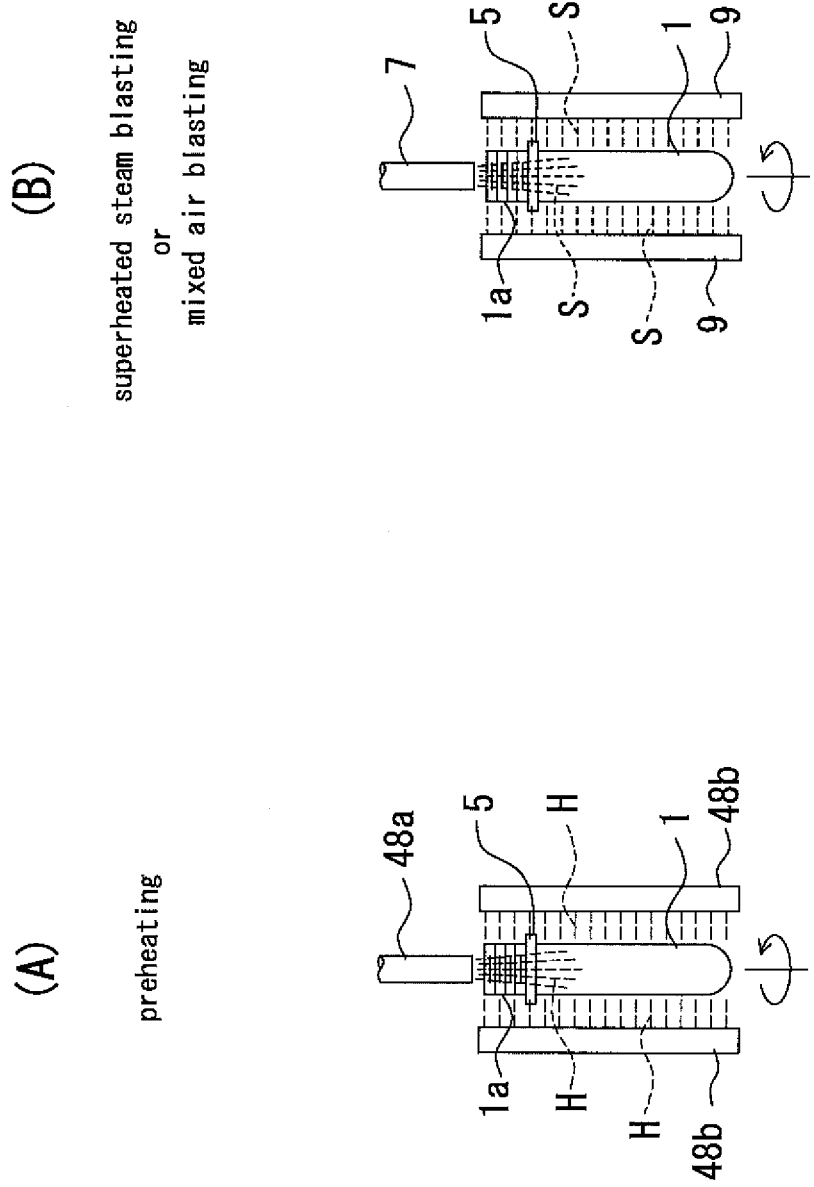
FIG. 6 is an explanatory view explaining the preform preheating process and a superheated steam blasting process or mixed air blasting process.

As shown in FIG. 6 (A), preheating is performed to the inner and outer surfaces of the preform 1 by blasting the aseptic hot air H to the entire inner and outer surfaces of the preform 1 including the mouth portion 1a thereof.

It is preferred that the temperature of the hot air H blasted to the preform 1 is 80° C. to 130° C., and more preferably, 90° C. to 120° C. In the temperature range of 80° C. to 130° C., only the surface of the preform 1 can be preheated to a temperature of 50° C. to 70° C., and in the temperature of the hot air H is less than 800° C., long blasting time is required for the preheating. Moreover, in the temperature of more than 130° C., the PET forming the preform 1 is itself overheated for a short time, and the preform 1, particularly, its mouth portion 1a, will become easily deformable.

Further, it may be possible to preheat only the inner surface of the preform 1.

The aseptic hot air H mentioned above may be generated by a hot air generating unit as shown in FIG. 5.

The hot air generating unit is provided, as an aseptic hot air (H) supply source, with a blower 45, a sterilization filter 46 and an electric heater 47. An outdoor air taken through the blower 45 is sterilized by the sterilization filter 46 and then heated by the electric heater 47 to a predetermined temperature. Thereafter, the aseptic heated wind is sent to the respective preheating nozzles 48a, 48b through conduits or ducts.

Further, it may be possible to preheat and humidify air by adding heated steam to the air flowing toward the sterilization filter 46 from the blower 45 to thereby enhance heat capacity of the aseptic hot air H from the electric heater 47. Moreover, the sterilization filter 46 may be composed of a pre-filter and an ULPA filter which are connected in series. By providing the pre-filter, the life time of the ULPA filter may be elongated.

A preheating nozzle denoted with reference numeral 48a is formed as a tubular nozzle. Such tubular nozzle is arranged such that an opening 49 thereof is directed perpendicularly downward.

The preform 1 is conveyed in one direction just below the circular opening 49 of the preheating nozzle 48a in an elected posture with the mouth portion 1a of the preform 1 being directed upward. A conveying mode may be a continuously conveying mode in which the preforms 1 are continuously conveyed or an intermittently conveying mode in which the preform 1 is temporality stops just below the opening 49 of the tubular nozzle 48a. The preform 1 can be conveyed with the support ring 5 of the preform 1 being clamped by a clamper, not shown.

Furthermore, a preheating nozzle denoted with reference numeral 48b is formed as a slit-shaped nozzle. Such preheating nozzle 48a is connected to a branch pipe of the conduit mentioned above in a manner such that a slit 50 of the nozzle 48a faces the side surface of the preform 1. It is desired to arrange a pair of preheating nozzles 48b in an opposing manner so as to clamp the preform 1 from both sides thereof. The preform 1 is conveyed while being rotated about its own axis. Although the preform 1 may be conveyed without being rotated, in such case, a plurality of preheating nozzles 48b may be arranged.

In the illustrated embodiment, although the preheating nozzle 48b is a slit-shaped nozzle, a plurality of circular nozzles such as tubular nozzles mentioned above may be arranged in the opposing manner to the side surface or bottom surface of the preform 1.

When the preform 1 is required to be sterilized, the aseptic hot air H is always supplied to the preheating nozzles 48a and 48b from the hot air generating unit and jetted toward the preform 1 from the circular opening 49 of the preheating nozzle 48a and the slit 50 of the preheating nozzle 48b. The diameters of the nozzles, angles, axis of the preform 1 are optional and are preliminarily set such that the jetted hot air H contact the entire surface of the preform 1.

According to the structure mentioned above, the hot air H jetted from the opening 49 of the preheating nozzle 48a enters inside of the preform 1 through the mouth portion 1a thereof and then contacts the entire inner surface thereof to thereby preheat the inner surface at the above-mentioned predetermined temperature.

On the other hand, the hot air H jetted from the slit 50 of the preheating nozzle 48$b$ contacts the entire outer surface including the mouth portion 1$a$ of the preform 1 now rotating about its axis to thereby preheat the entire outer surface to the above-mentioned predetermined temperature.

Next, as shown in FIG. 6(B) and FIG. 1, the entire surface of the preheated preform 1 is subjected to the sterilization treatment. That is, this sterilization treatment is performed by blasting the superheated steam S, having pressure higher than the atmospheric pressure, generated from water having temperature of 200° C. to 700° C. to the entire inner and outer surfaces of the preform 1 including the mouth portion 1$a$.

A temperature for blasting the superheated steam S to the preform 1 is preferably of 200° C. to 700° C., and more preferably, 250° C. to 500° C. Within the temperature range of 200° C. to 700° C., only the surface of the preform is exposed to high temperature, and thereby, fungus or like adhering to the surface of the preform 1 can be sterilized for a short time. In the case of the temperature of the superheated steam S of less than 200° C., long time blasting of the superheated steam S is required for the sterilization, which will result in temperature increase of the PET itself constituting the preform 1, which leads to the deformation of the preform. In the case of more than 700° C., the temperature of the PET will be increased for a short time, which will lead to easy deformation of the preform 1.

A pressure of the superheated steam S to be blasted to the preform 1 is higher than the atmospheric pressure, and is preferably more than 0.1 MPa and less than 0.3 MPa. In a case where this pressure is near 0.1 MPa, even if the superheated steam S contacts the preform and the temperature thereof is lowered, there is less possibility of condensation (bedewing), and in a case where this pressure is more than 0.3 MPa, when the superheated steam S is blasted to the preform 1, the condensation thereof may be formed on the surface of the preform 1. When such condensation is formed, there may cause a fear of generating whitening to the surface of the bottle 2 at the time of blow-molding the preform into a bottle or like.

Furthermore, it is preferred that the time for blasting the superheated steam S to the preform 1 is within 1.0 to 3.0 sec. In the case of less than 1.0 sec., defective sterilization may be likely caused, and in the case of more than 3.0 sec., the mouth portion 1$a$ of the preform 1 may be likely deformed. Because the surface of the preform 1 is preliminarily heated as mentioned above, this superheated steam blasting time can be shortened by 2.0 to 4.0 sec. as compared with a case of no preheating process.

Further, it is essential to sterilize the inner surface of the preform 1, but the sterilization of the outer surface thereof may be performed by the heating at the time of blow-molding treatment, which will be mentioned hereinafter. Otherwise, it may be possible to add a desired sterilizing treatment after the blow-molding treatment.

The superheated steam S will be obtainable by using an apparatus similar to the superheated steam generator 12 used in the first embodiment 1.

The above-mentioned preform sterilizing method may be incorporated in the inline system represented by FIG. 6(A), (B), FIG. 2(B), (C), and FIG. 3(D), (E), (F), thereby manufacturing a lot of aseptic packaged products.

In such inline system, the preforms 1 are continuously conveyed at the desired conveying speed and are formed as aseptic packaged products through the respective processes or treatments shown in FIG. 6(A), (B), FIG. 2(B), (C), and FIG. 3(D), (E), (F).

First, as shown in FIG. 5 and FIG. 6(A), the preform 1 passes a position, at which the tubular nozzle and the slit-shaped nozzle as the preheating nozzles 48$a$ and 48$b$ are disposed, at a predetermined travelling speed while being travelled with its vertically elected posture being maintained. During this passing, as mentioned above, the aseptic hot air H is blasted into the interior of the preform 1 through the mouth portion 1$a$ and also blasted to the outer surface thereof, so that the entire surface including inner and outer surfaces of the preform 1 can be preheated for a short time.

In the illustrated example, although when the hot air is blasted, the preform 1 is maintained in its vertically elected posture, it may be possible for the preform 1 to have its inverted posture.

Subsequently, as shown in FIG. 1 and FIG. 6(B), the preform 1 passes a position, at which the tubular nozzle and the slit-shaped nozzle as the sterilizing nozzles 7 and 9 are disposed, at a predetermined travelling speed while being travelled with its vertically elected posture being maintained. During this passing, as mentioned above, the superheated steam S is blasted into the interior of the preform 1 through the mouth portion 1$a$ and also blasted to the outer surface thereof, so that the entire surface including inner and outer surfaces of the preform 1 can be sterilized for a short time.

In the illustrated example, although when the superheated steam S is blasted, the preform 1 is maintained in its vertically elected posture, it may be possible for the preform 1 to have its inverted posture.

Since such sterilization as described above is performed for a short time, the mouth portion 1$a$ of the preform 1 is free from deformation and resin material forming the preform 1 is not excessively heated. In addition, since steam drain is not dewed and does not remain on the surface of the preform 1, the bottle 2 molded in the blow-molding process performed thereafter is never whitened.

Further, the inner and outer surfaces of the preform 1 may be sterilized in a manner shifted in time by alternatively shifting the sterilizing nozzles 7 and 9 in arrangement.

As shown in FIG. 2(C), a heater 17 is disposed in a wall-like arrangement along the conveying path of the preform 1, and the preform 1 is heated, while travelling, by the heater 17 uniformly to a temperature of about 90° C. to 130° C. suitable for the subsequent blow-molding treatment.

In the heating period, a spindle 11 is inserted into the preform 1 through the mouth portion 1$a$ thereof with the preform 1 being suspended in the elected state and rotated together with the spindle 11 to be thereby uniformly heated by the heater 10.

The preform 1 heated to a temperature suitable for the blow-molding treatment is subjected to the blow-molding treatment as shown in FIG. 2(C), and then formed into the bottle 2 as a container as shown in FIG. 3(D).

In FIG. 2(C), a mold 12 as a blow-molding mold is continuously travelled at the same speed as the travelling speed of the preform 1, the preform 1 is clamped, the blow-molding is performed to the preform within the mold 12, and the mold 12 is thereafter opened.

The preform 1 has been heated substantially uniformly so that the entire temperature of the preform increases to a temperature range suitable for the molding treatment in the heating process shown in FIG. 2(B), and with this temperature being maintained, the preform 1 is inserted into the mold 12 together with the spindle 11 as shown in FIG. 2(C).

Further, a blow nozzle 13 is inserted into the preform 1 passing the upper portion of the mold 12 and penetrating the spindle 11 in the mouth portion 1a of the preform 1.

While travelling the mold 12, for example, primary air for blowing and secondary air for blowing are subsequently blasted into the preform 1 from the blow nozzle 13, and the preform 1 is thereby swelled in the cavity C of the mold 12 into the bottle 2 as final product.

When the bottle 2 is molded into the mold 12, the mold 12 is opened while travelling, and as shown in FIG. 3(D), the bottle 2 as final product is taken out of the mold 12.

After the molding treatment, the bottle 2 is continuously travelled, and thereafter, as shown in FIG. 3(E), an inner content a such as mineral water, tea containing catechin, carbonated drink, or like drink is filled into the bottle 2 through a filling nozzle 14, and as shown in FIG. 3(F), the bottle is sealed with the cap 4 as a lid.

Further, it may be preferred that the sterilizing effect is enhanced by sterilizing the outer surface of the bottle 2 by the spray of the steam including the sterilizing agent such as hydrogen peroxide or irradiation of electron ray or like to the bottle 2 after the blow-molding treatment. In a case where the inner surface of the bottle is sterilized by spraying the hydrogen peroxide, it is necessary to passively reduce concentration of the hydrogen peroxide to eliminate possibility of remaining of the hydrogen peroxide inside the bottle.

After the above treatments, the bottles 2 produced as packaged products are collected and transported to markets.

Figure 7:
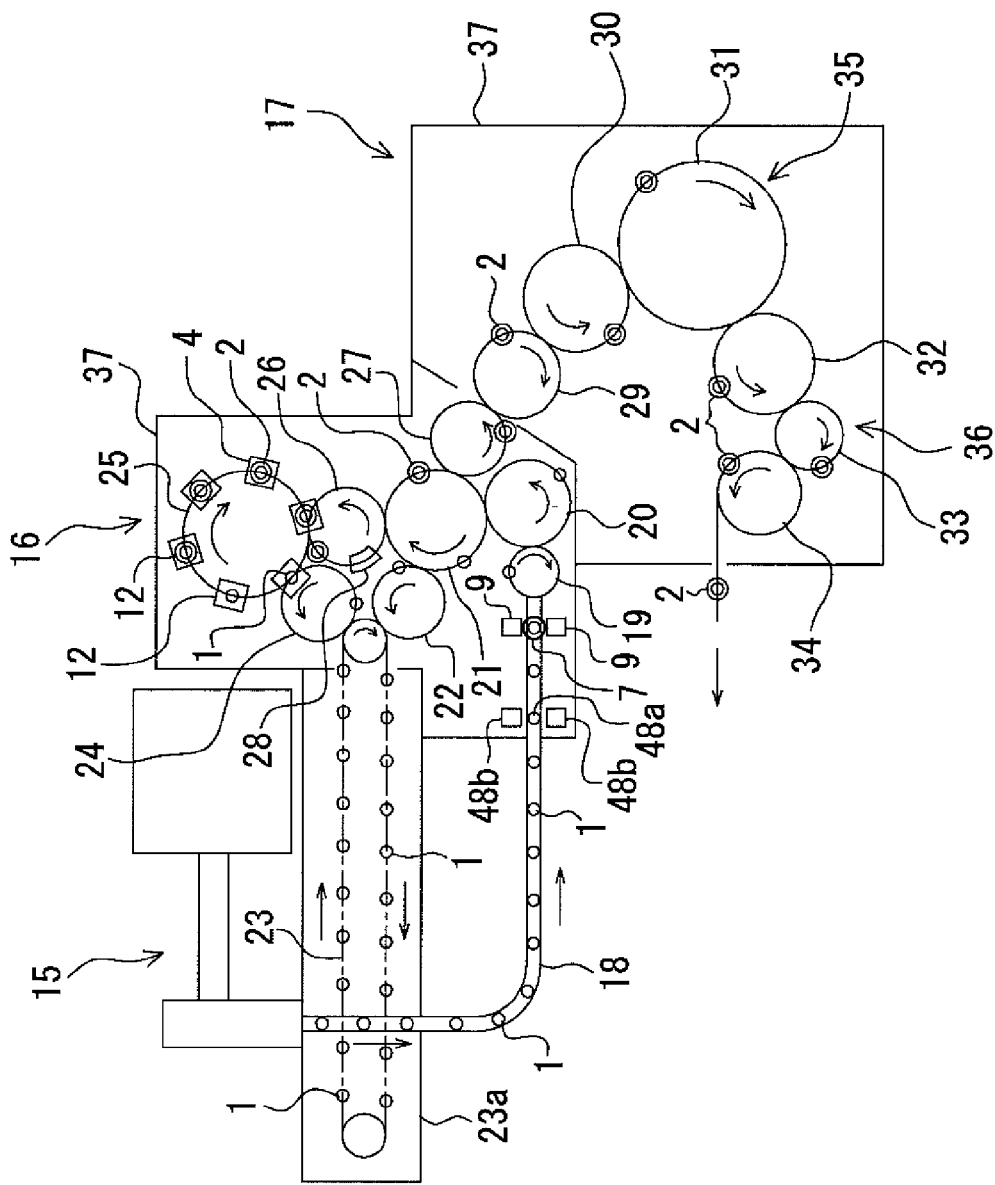
FIG. 7 is a schematic plan view showing another embodiment of an inner content filling machine.

A filling system for effecting the filling method mentioned above has a configuration or structure such as shown in FIG. 7, for example.

As shown in FIG. 7, although this filling system has substantially the same structure as that of the first embodiment 1 shown in FIG. 4, it differs from the first embodiment 1 in that preheating nozzles 48a, 48b for blasting the aseptic hot air H toward the preform 1 are disposed to portions slightly upstream side than a portion at which the preform conveyer 18 in the preform supplying machine 15 is connected to the wheel 19. The aseptic hot air H is blasted toward the preform 1 from these nozzles 48a, 48b (see FIG. 5 and FIG. 6(A)), thereby uniformly preheating the inner and outer surfaces of the preform 1.

Furthermore, the sterilizing nozzles 7 and 9 for jetting the superheated steam S toward the preform 1 are disposed in a manner adjacent to each other from the downstream side of the preheating nozzles 48a, 48b. The superheated steam S is blasted toward the surface of the preheated preform 1 (see FIG. 1 and FIG. 6(B)), thereby uniformly sterilizing the inner and outer surfaces of the preform 1.

It is further to be noted that the preheating nozzles 48a, 48b, and the sterilizing nozzles 7, 9 may be disposed to predetermined positions on the outer periphery of the wheels 21 and 22, and for example, disposed on the front side of a position to which the preform 1 reaches the conveyer 23.

EXAMPLE 5

Superheated steam made by heating water and generated by a superheated steam generator of induction heating system and then blasted toward inner surfaces of preforms for 500 mL (milliliter) PET bottle and 2 L (litter) PET bottle through the nozzles each having an inner diameter of 8 mmφ at flow rate of 0.7/sec. with blasting temperature of 300° C.

In such spraying, the sterilizing effect was confirmed as shown in Table 7 in an evaluation with indicating bacillus inoculated on the inner surface of the preforms.

TABLE 7

| Bottle Volume | Preheating Temperature | Steam Blasting Time | B. sub | A. niger |
|---|---|---|---|---|
| 500 mL | No | 4.5 sec. | 3.1D | 4.3D |
| | No | 5.0 sec. | 3.1D | More than 6.0D |
| | 90° C. | 1.0 sec. | 3.0D | More than 6.0D |
| 2 L | No | 4.5 sec. | 3.1D | 4.8D |
| | No | 5.0 sec. | 3.1D | More than 6.0D |
| | 90° C. | 1.0 sec. | 3.0D | More than 6.0D |

In the above Table 7, term "B.sub." is an abbreviated term of "Bacillus subtilis", and "A.nig." is an abbreviated term of "Aspergillus niger". "D" is a D-valve indicating the sterilizing effect. The preheating temperature is a temperature on the inner surface of the preform.

As is apparent from the Table 7, when it is required to obtain a sterilizing effect more than 6.0 D with respect to the A. niger, in a case when the preform for the PET bottle was preheated, the superheated steam blasting time could be reduced by ⅕ time in comparison with a case of performing no preheating treatment.

<Embodiment 4>

Hereunder, a fourth embodiment 4 of the present invention will be explained.

As shown in FIG. 5, the preheating to the preform is performed by blasting the aseptic hot air H to the entire inner and outer surfaces of the preform 1 including the mouth portion 1a.

A temperature for blasting the superheated steam S to the preform 1 is preferably of 80° C. to 130° C., and more preferably, 90° C. to 120° C. Within the temperature range of 80° C. to 130° C., only the surface of the preform is preheated to a temperature of 50° C. to 70° C. In the case of the temperature of less than 80° C., long time blasting of the superheated steam S is required for the sterilization. In the case of more than 130° C., the temperature of the PET will be increased for a short time, which will lead to easy deformation of the preform 1, and particularly, the mouth portion 1a thereof.

Further, the preheating of the preform 1 may be performed only to the inner surface of the preform 1.

The hot air H blasted through the opening 10 of the preheating nozzle 9a enters inside the preform 1 through the mouth portion 1a thereof and contacts the entire inner surface of the preform 1 to thereby preheat the entire inner surface of the preform 1 to the predetermined temperature.

Moreover, the hot air H blasted through the slit 11 of the preheating nozzle 9b contacts the entire outer surface of the preform including the mouth portion 1a rotating around its axis to thereby preheat the entire outer surface of the preform 1 to the predetermined temperature.

Next, as shown in FIG. 1, the entire surface of the thus preheated preform 1 is subjected to the sterilization treatment. That is, this sterilization treatment is performed by blasting the superheated steam S generated from water mixed with hydrogen peroxide having concentration of 0.5% to 15% and having a temperature of 150° C. to 500° C. and a pressure higher than the atmospheric pressure.

A temperature for blasting the superheated steam S to the preform 1 is preferably of 150° C. to 500° C., and more preferably, 250° C. to 400° C. Within the temperature range of 150° C. to 500° C., by exposing only the surface of the preform 1 to a high temperature, the fungus adhering to the surface of the preform 1 can be sterilized for a short time. In the case of the temperature of less than 150° C., long time blasting of the superheated steam S is required for the sterilization and the PET forming the preform 1 is itself highly heated, leading to large deformation of the preform 1. In the case of more than 500° C., the temperature of the PET forming the preform 1 is itself increased even for a short time, which will lead to easy deformation of the preform 1.

A pressure of the superheated steam to be blasted to the preform 1 is higher than atmospheric pressure, and is preferably more than 0.1 MPa and less than 0.3 MPa. In a case where this pressure is near 0.1 MPa, even if the superheated steam contacts the preform and the temperature thereof is lowered, there is less possibility of condensation (bedewing), and in a case where this pressure is more than 0.3 MPa, when the superheated steam is blasted to the preform 1, the condensation thereof may be formed on the surface of the preform 1. When such condensation is formed, there may cause a fear of generating whitening to the surface of the bottle 2 at the time of blow-molding the preform into a bottle or like.

Furthermore, it is preferred that the time for blasting the superheated steam S to the preform 1 is within 1.0 to 3.0 sec. In the case of less than 1.0 sec., defective sterilization may be likely caused, and in the case of more than 3.0 sec., the mouth portion 1a of the preform 1 may be likely deformed. This superheated steam blasting time can be reduced by 2.0 to 4.0 sec. because of the preheating of the surface of the preform 1 in comparison with a case of no preheating treatment.

Further, although it is essential for the inner surface of the preform 1 to be sterilized, it may be possible for the outer surface thereof to perform the sterilization by the heating for the blow-molding treatment, mentioned hereinlater, or may be possible to add a required sterilization treatment after the blow-molding treatment.

The preheated preform 1 is conveyed in one direction just below the circular opening 15 of the sterilizing nozzle 13a in an elected posture with the mouth portion 1a of the preform 1 being directed upward. A conveying mode may be a continuously conveying mode in which the preforms 1 are continuously conveyed or an intermittently conveying mode in which the preform 1 is temporally stops just below the opening 15 of the sterilizing nozzle 13a. The preform 1 can be conveyed with the support ring 5 of the preform 1 being clamped by a clamper, not shown.

When the preform 1 is sterilized, the superheated steam S generated from water mixed with the hydrogen peroxide having concentration of 0.5% to 15%, that is, the superheated steam S as a mixture of the hydrogen peroxide and water, is always supplied to the sterilizing nozzles 13a, 13b from the superheated steam generator 12, and such superheated steam S jetted toward the preform 1 from the circular opening 15 of the sterilizing nozzle 13a and from the slit 16 of the other sterilizing nozzle 13b. The nozzle diameter, an angle, an axis of the preform 1 are optional, which are preliminarily set so that the jetted superheated steam S contacts the entire inner surface of the preform 1.

According to the manner mentioned above, the superheated steam S jetted from the opening 15 of the sterilizing nozzle 13a enters inside the preform 1 through the mouth portion 1a thereof and then contacts the entire inner surface of the preform to thereby sterilize the general bacteria, fungus, yeast and the like adhering to the inner surface of the preform 1. Moreover, since the hydrogen peroxide of 0.5% to 15% concentration is mixed with this superheated steam S, the spore-forming bacteria can be also sterilized. In addition, since it is possible to perform such sterilization treatment for a short time by blasting the superheated steam S toward the interior of the preform 1, excessive heating from the inside of the mouth portion 1a of the preform 1 can be avoided, the deformation of the mouth portion 1a can be surely prevented.

Furthermore, on the other hand, the superheated steam S jetted from the slit 16 of the other sterilizing nozzle 13b contacts the entire outer surface including the mouth portion 1a of the preform 1 rotating around its axis to thereby heat and sterilize the outer surface of the preform 1 to thereby sterilize the general bacteria, fungus, yeast and the like, as well as the spore-forming bacteria adhering to the outer surface of the preform 1. Moreover, since it is possible to perform such sterilization treatment for a short time by blasting the superheated steam S toward the outer of the preform 1, excessive heating from the outside of the mouth portion 1a of the preform 1 can be avoided, and hence, the deformation of the mouth portion 1a can be surely prevented.

The above-mentioned preform sterilizing method may be incorporated in the inline system represented by FIG. 6(A), (B), FIG. 2(B), (C), and FIG. 3(D), (E), (F), thereby obtaining a lot of aseptic packaged products.

In such inline system, the preforms 1 are continuously conveyed at the desired conveying speed and are formed as aseptic packaged products through the respective processes or treatments shown in FIG. 6(A), (B), FIG. 2(B), (C), and FIG. 3(D), (E), (F).

First, as shown in FIG. 6(A), the preform 1 passes a position, at which the tubular nozzle and the slit-shaped nozzle as the preheating nozzles 48a and 48b are disposed, at a predetermined travelling speed while being travelled with its vertically elected posture being maintained. During this passing, as mentioned above, the aseptic hot air H is blasted into the interior of the preform 1 through the mouth portion 1a and also blasted to the outer surface thereof, so that the entire surface including inner and outer surfaces of the preform 1 can be preheated for a short time.

In the illustrated example, although when the hot air is blasted, the preform 1 is maintained in its vertically elected posture, it may be possible for the preform 1 to have its inverted posture.

Subsequently, as shown in FIG. 6(B), the preform 1 passes a position, at which the tubular nozzle and the slit-shaped nozzle as the sterilizing nozzles 7 and 9 are disposed, at a predetermined travelling speed while being travelled with its vertically elected posture being maintained. During this passing, as mentioned above, the superheated steam S, that was generated from the water mixed with the hydrogen peroxide of 0.5% to 15% concentration, is blasted into the interior of the preform 1 through the mouth portion 1a, and the same superheated steam S is also blasted to the outer surface thereof, so that the entire surface including inner and outer surfaces of the preform 1 can be sterilized for a short time.

In the illustrated example, although when the superheated steam S is blasted, the preform 1 is maintained in its vertically elected posture, it may be possible for the preform 1 to have its inverted posture.

Since such sterilization as described above is performed for a short time, the mouth portion 1a of the preform 1 is free from deformation and the resin material forming the preform 1 is not excessively heated. In addition, since steam drain is not dewed and does not remain on the surface of the preform 1, the bottle 2 molded in the blow-molding process performed thereafter is never whitened.

Further, the inner and outer surfaces of the preform 1 may be sterilized in a manner shifted in time by alternatively shifting the sterilizing nozzles 7 and 9 in arrangement.

As shown in FIG. 2(B), a heater 10 is disposed in a wall-like arrangement along the conveying path of the preform 1, and the preform 1 is heated, while travelling, by the heater 10 uniformly to a temperature of about 90° C. to 130° C. suitable for the subsequent blow-molding treatment.

In the heating period, a spindle 11 is inserted into the preform 1 through the mouth portion 1a thereof with the preform 1 being suspended in the elected state and rotated together with the spindle 11 to be thereby uniformly heated by the heater 10.

The preform 1 heated to a temperature suitable for the blow-molding treatment is subjected to the blow-molding treatment as shown in FIG. 2(C), and then formed into the bottle 2 as a container as shown in FIG. 3(D).

In FIG. 2(C), a mold 12 as a blow-molding mold is continuously travelled at the same speed as the travelling speed of the preform 1, the preform 1 is clamped, the blow-molding is then performed to the preform 1 within the mold 12, and the mold 12 is thereafter opened.

The preform 1 has been heated substantially uniformly so that the entire temperature of the preform increases to a temperature range suitable for the molding treatment in the heating process shown in FIG. 2(B), and with this temperature being maintained, the preform 1 is inserted into the mold 12 together with the spindle 11 as shown in FIG. 2(C). Further, a blow nozzle 13 is inserted into the preform 1 passing the upper portion of the mold 12 and penetrating the spindle 11 in the mouth portion 1a of the preform 1.

During the travelling of the mold 12, for example, primary air for blowing and secondary air for blowing are subsequently blasted into the preform 1 from the blow nozzle 13, and the preform 1 is thereby swelled in the cavity C of the mold 12 into the bottle 2 as final product.

When the bottle 2 is molded into the mold 12, the mold 12 is opened while travelling, and as shown in FIG. 3(D), the bottle 2 as final product is taken out of the mold 12.

After the molding treatment, the bottle 2 is continuously travelled, and thereafter, as shown in FIG. 3(E), an inner content a such as mineral water, tea containing catechin, carbonated drink, or like drink is filled into the bottle 2 through a filling nozzle 14, and as shown in FIG. 3(F), the bottle is sealed with the cap 4 as a lid.

Further, it may be preferred that the sterilizing effect is enhanced by sterilizing the outer surface of the bottle 2 by the spray of the steam including a sterilizing agent such as hydrogen peroxide or irradiation of electron ray or like to the bottle 2 after the blow-molding treatment. In a case where the inner surface of the bottle is sterilized by spraying the hydrogen peroxide, it is necessary to passively reduce concentration of the hydrogen peroxide to eliminate possibility of remaining of the hydrogen peroxide inside the bottle.

After the above treatments, the bottles 2 produced as packaged products are collected and transported to markets.

A filling system for performing the filling method mentioned above has a configuration or structure such as shown in FIG. 7, for example.

EXAMPLE 6

Water mixed with the hydrogen peroxide of 3.0% concentration was heated by a superheated steam generator of induction heating system to thereby generate the superheated steam, which was then splayed to the inner surface of each preform for 500 mL PET bottle and 2 L PET bottle from a nozzle having inner diameter of 8 mmΦ at flow rate of 0.7 g/sec.

In such spraying, the sterilizing effect was confirmed as shown in Table 8 in an evaluation with indicating bacillus inoculated on the inner surface of the preforms.

TABLE 8

| Bottle Volume | Preheating Temperature | Steam Blasting Time | B. sub | A. niger |
|---|---|---|---|---|
| 500 mL | No | 4.5 sec. | 3.1D | More than 6.0D |
|  | No | 5.0 sec. | 6.0D | More than 6.0D |
|  | 90° C. | 1.0 sec. | More than 6.3D | More than 6.2D |
| 2 L | No | 4.5 sec. | 3.0D | More than 6.0D |
|  | No | 5.0 sec. | 5.8D | More than 6.0D |
|  | 90° C. | 1.0 sec. | More than 6.8D | More than 6.2D |

In the above Table 8, term "*B.sub.*" is an abbreviated term of "*BaciLLus subtiLis*", and "*A.nig.*" is an abbreviated term of "*AspergiLLus niger*". "D" is a D-valve indicating the sterilizing effect. The preheating temperature is a temperature on the inner surface of the preform.

As is apparent from the Table 8, when it is required to obtain a sterilizing effect more than 6.0 D with respect to the *A. niger*, in a case when the preform for the PET bottle was preheated, the superheated steam blasting time could be reduced by ⅕ compared with a case of performing no preheating, and in addition, the sterilization to the spore-forming bacteria could be performed.

<Embodiment 5>

In this embodiment 5, the superheated steam S is blasted into the preform 1 through the nozzle 7 while the nozzle 7 being relatively inserted into the preform 1.

Figure 8:
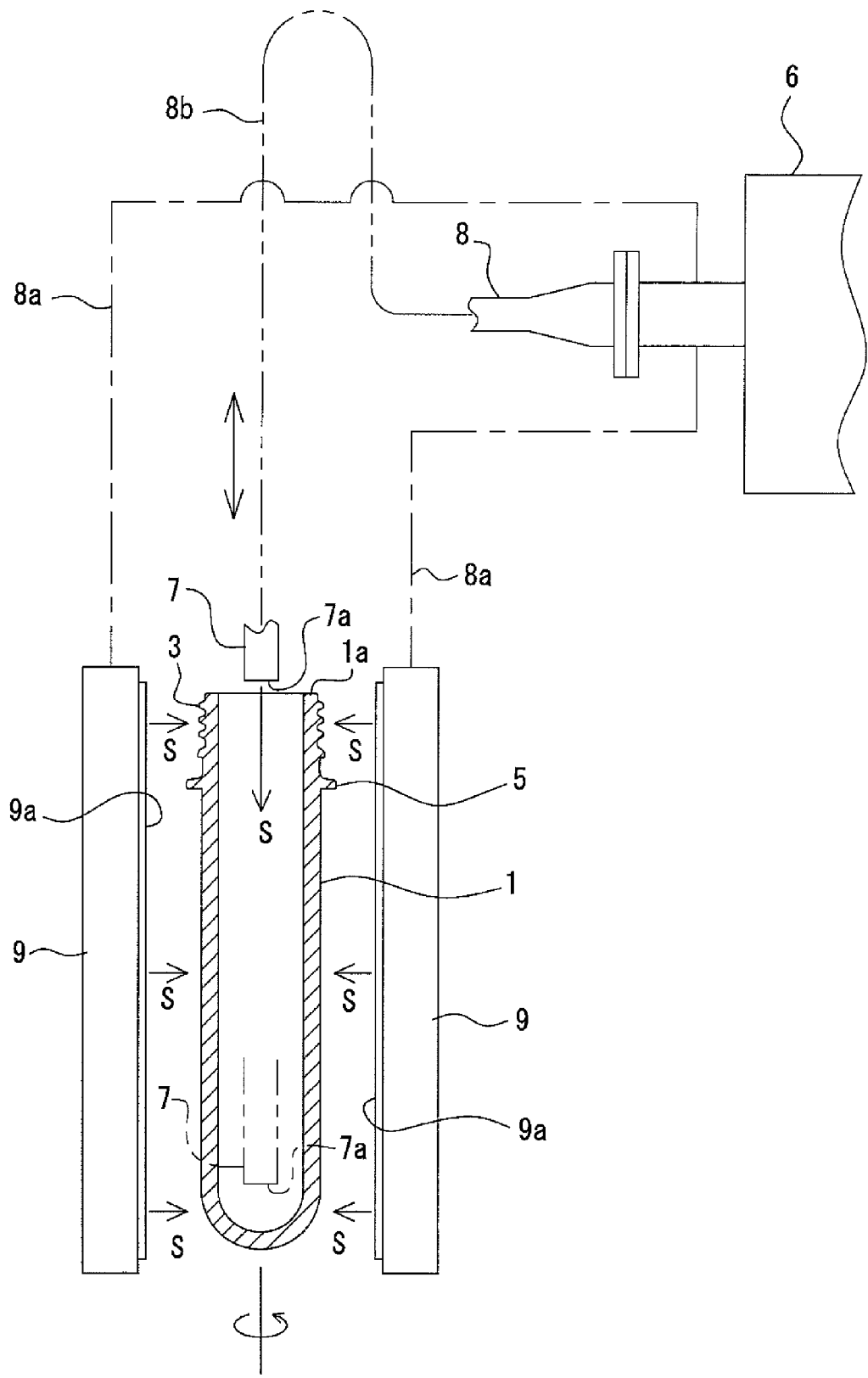
FIG. 8 is an explanatory view showing another embodiment of a preform sterilizing method according to the present invention.

As shown in FIG. 8, a flexible tube 8b is disposed between the tubular nozzle 7 and the conduit 8 on the superheated steam generator (6) side. The tubular nozzle 7 is reciprocally movable in a slidable manner in the vertical direction by a driving means such as guide means or piston-cylinder assembly, both not shown.

The preform 1 is conveyed in one direction just below the circular opening 7a of the tubular nozzle 7 in the elected posture with the mouth portion 1a thereof being directed upward. The preform 1 can be conveyed with the support ring 5 thereof being clamped by a clamper.

In a case where the intermittent conveying mode is adopted as the conveying mode, every time when the preform 1 stops just below the opening 7a of the tubular nozzle 7, the tubular nozzle 7 is lowered into the preform 1 to a position near the bottom thereof by the driving means. At this instance, the flexible tube 8b is preferably flexed so as not to disturb the movement of the tubular nozzle 7. The superheated steam is blasted through the opening 7a of the tubular nozzle 7 while lowering inside the preform 1.

Accordingly, the superheated steam S contacts uniformly the entire inner and outer surfaces of the preform 1, thereby more smoothly and promptly sterilizing the general bacteria, fungus, yeast or like adhering to the inner surface of the preform 1.

Further, in the case where the continuous conveying mode, in which the preforms 1 are continuously travelled, is adopted as the conveying mode, a number of tubular nozzles 7 and the flexible tubes 8b are arranged in synchronism with the travelling of the preforms 1 in a swingably movable manner. In addition, a rotary joint, not sown, for smoothly supplying the superheated steam to the respective tubular nozzles 7 from the superheated steam generator 6 is provided between the superheated steam generator 6 and the conduit 8.

Furthermore, the sterilization of the general bacteria, fungus, yeast or like adhering to the outer surface of the preform 1 is performed by the superheated steam S jetted from the slit 9a of the slit-shaped nozzle 9.

<Embodiment 6>

Figure 9:
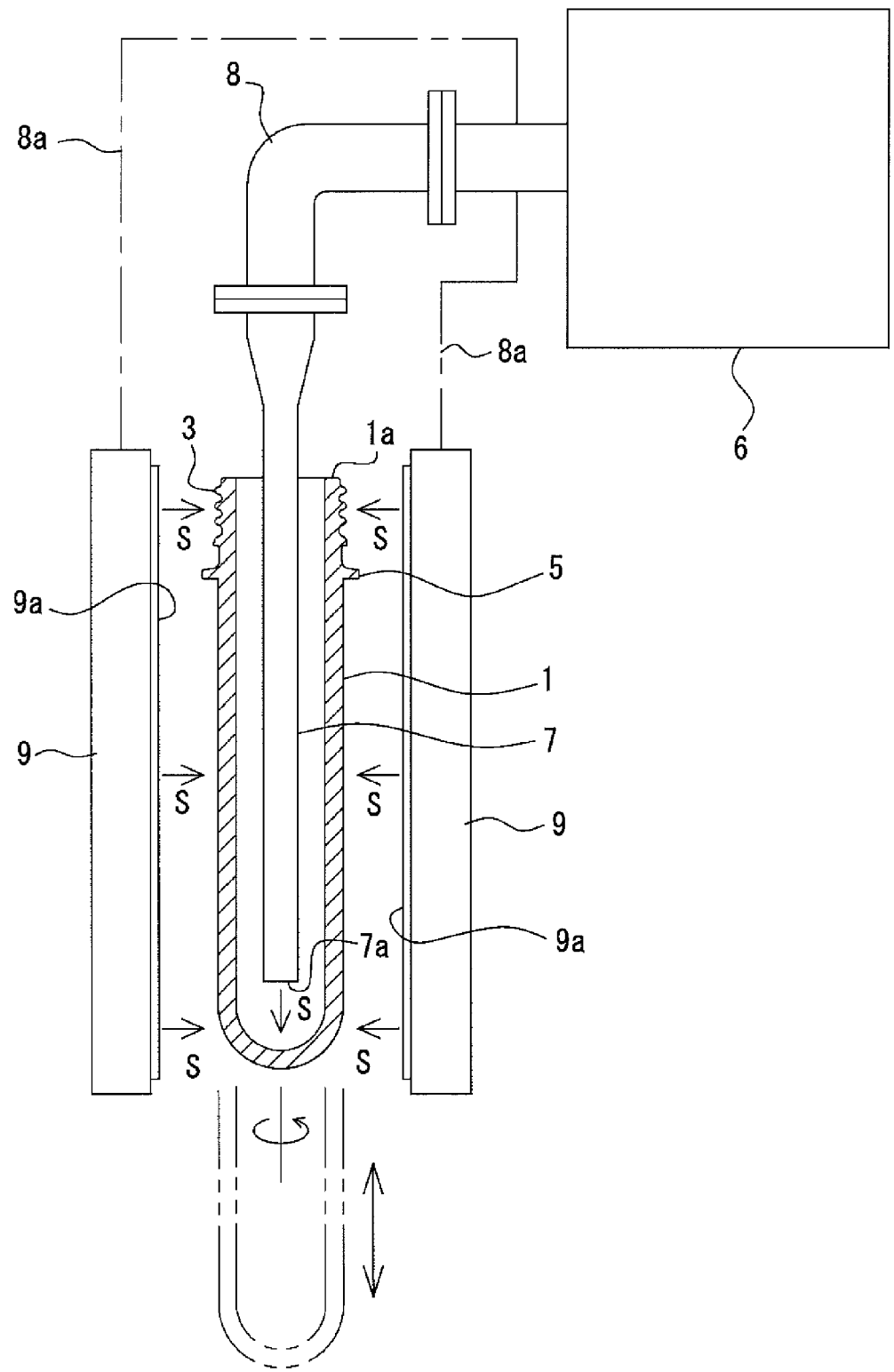
FIG. 9 is an explanatory view showing a further embodiment of a preform sterilizing method according to the present invention.

As shown in FIG. 9, in this sixth embodiment 6, the tubular nozzle 7 is formed so as to have a length capable of reaching a position near the bottom of the preform 1.

The preform 1 is conveyed just below the opening 7a of the tubular nozzle 7 in the elected posture with the mouth portion 1a thereof being directed upward.

The preform 1 can be conveyed with the support ring 5 thereof being clamped by the clamper, not shown. This clamper may be reciprocally movable in the vertical direction by a piston-cylinder assembly, not shown.

In the case where the intermittent conveying mode is adopted as conveying mode for the preform 1, every time when the preform 1 is temporarily stopped just below the opening 7a of the tubular nozzle 7, the clamper is raised upward with the preform being held, and as sown in FIG. 9, the tubular nozzle 7 is inserted into the preform so that the opening 7a of the tubular nozzle 7 reaches a position near the bottom of the preform 1. The tubular nozzle 7 jets the superheated steam through the opening 7a thereof while being relatively lowered inside the preform 1.

According to such motion, the superheated steam S contacts uniformly the entire inner surface of the preform 1, and the general bacteria, fungus, yeast and the like adhering to the inner surface of the preform 1 can be more smoothly and promptly sterilized.

Further, in the case where the continuous conveying mode, in which the preforms 1 are continuously travelled, is adopted as the conveying mode, a number of tubular nozzles 7 are arranged in synchronism with the travelling of the preforms 1 in a swingably movable manner. In addition, a rotary joint, not sown, for smoothly supplying the superheated steam to the respective tubular nozzles 7 from the superheated steam generator 6 is provided between the superheated steam generator 6 and the conduit 8.

Furthermore, the sterilization of the general bacteria, fungus, yeast and the like adhering to the outer surface of the preform 1 can be performed by the superheated steam S jetted from the slit 9a of the slit-shaped nozzle 9.

REFERENCE NUMERAL

1 —preform
1a —mouth portion
2 —container
4 —lid
6 —superheated steam generator
7 —sterilizing nozzle
10 —heater
12 —blow-molding mold
35 —filler
36 —capper
48a —preheating nozzle
S —superheated steam
a —inner content
H —hot air

The invention claimed is:

1. A method for sterilizing a preform formed into a bottle by blow molding, wherein superheated steam generated from water, and having a temperature of 200° C. to 500° C. and a pressure higher than 0.1MPa and less than 0.3MPa is blasted to at least an inner surface of an entire surface of a preform formed into a bottle by blow molding including a mouth portion thereof.

2. The preform sterilizing method according to claim 1, wherein the superheated steam is generated by induction-heating the water.

3. The preform sterilizing method according to claim 2, wherein the sterilization of the inner surface of the preform is performed by blasting the superheated steam into the preform through a nozzle disposed oppositely to the mouth portion of the preform, and a flow rate of the superheated steam is set to a level so as not to deform the mouth portion of the preform.

4. The preform sterilizing method according to claim 2, wherein the superheated steam, that was generated from the water mixed with a hydrogen peroxide of 0.5% to 15% concentration, and having a temperature of 150° C. to 500° C. and a pressure higher than 0.1MPa and less than 0.3MPa is blasted to at least the inner surface of the entire surface of the preform including a mouth portion thereof.

5. The preform sterilizing method according to claim 2, wherein an aseptic hot air is blasted to at least the inner surface of the entire surface of the preform including a mouth portion thereof to preheat the inner surface, and the superheated steam is then blasted to at least the inner surface.

6. The preform sterilizing method according to claim 1, wherein the sterilization of the inner surface of the preform is performed by blasting the superheated steam into the preform through a nozzle disposed oppositely to the mouth portion of the preform, and a flow rate of the superheated steam is set to a level so as not to deform the mouth portion of the preform.

7. The preform sterilizing method according to claim 6, wherein the superheated steam, that was generated from the water mixed with a hydrogen peroxide of 0.5% to 15% concentration, and having a temperature of 150° C. to 500° C. and a pressure higher than 0.1MPa and less than 0.3MPa is blasted to at least the inner surface of the entire surface of the preform including a mouth portion thereof.

8. The preform sterilizing method according to claim 6, wherein an aseptic hot air is blasted to at least the inner surface of the entire surface of the preform including a mouth portion thereof to preheat the inner surface, and the superheated steam is then blasted to at least the inner surface.

9. The preform sterilizing method according to claim 1, wherein the superheated steam, that was generated from the water mixed with a hydrogen peroxide of 0.5% to 15% concentration, and having a temperature of 150° C. to 500° C. and a pressure higher than 0.1MPa and less than 0.3MPa is blasted to at least the inner surface of the entire surface of the preform including a mouth portion thereof.

10. The preform sterilizing method according to claim 9, wherein an aseptic hot air is blasted to at least the inner surface of the entire surface of the preform including a mouth portion thereof to preheat the inner surface, and the superheated steam is then blasted to at least the inner surface.

11. The preform sterilizing method according to claim 1, wherein an aseptic hot air is blasted to at least the inner surface of the entire surface of the preform including a mouth portion thereof to preheat the inner surface, and the superheated steam is then blasted to at least the inner surface.

12. An inner content filling method comprising the steps of, while continuously conveying preforms: sterilizing at least an inner surface of each preform: heating the sterilized preform to a temperature suitable for molding the preform: forming a container by blow-molding the preform in a blow-molding mold that is also continuously travelled: filing the molded container with an inner content: and then sealing the container with a lid, wherein the sterilization of the preform is performed by blasting superheated steam having a temperature of 200° C. to 500° C. and a pressure higher than 0.1MPa and less than 0.3MPa is blasted to at least an inner surface of an entire surface of a preform including a mouth portion thereof.

13. The inner content filling method according to claim 12, wherein the superheated steam, that was generated from the water mixed with a hydrogen peroxide of 0.5% to 15% concentration, and having a temperature of 150° C. to 500° C. and a pressure higher than 0.1MPa and less than 0.3MPa is blasted to at least the inner surface of the entire surface of the preform including a mouth portion thereof.

14. The inner content filling method according to claim 13, wherein an aseptic hot air is blasted to at least the inner surface of the entire surface of the preform including a mouth portion thereof to preheat the inner surface, and the superheated steam is then blasted to at least the inner surface.

15. The inner content filling method according to claim 12, wherein an aseptic hot air is blasted to at least the inner surface of the entire surface of the preform including a mouth portion thereof to preheat the inner surface, and the superheated steam is then blasted to at least the inner surface.

* * * * *